United States Patent
Blumenkranz et al.

(10) Patent No.: US 12,161,306 B2
(45) Date of Patent: Dec. 10, 2024

(54) SYSTEMS AND METHODS OF ACCESSING ENCAPSULATED TARGETS

(71) Applicant: INTUITIVE SURGICAL OPERATIONS, INC., Sunnyvale, CA (US)

(72) Inventors: Stephen J. Blumenkranz, Los Altos, CA (US); Federico Barbagli, San Francisco, CA (US); Christopher R. Carlson, Belmont, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 1179 days.

(21) Appl. No.: 16/484,047

(22) PCT Filed: Feb. 9, 2018

(86) PCT No.: PCT/US2018/017621
§ 371 (c)(1),
(2) Date: Aug. 6, 2019

(87) PCT Pub. No.: WO2018/148544
PCT Pub. Date: Aug. 16, 2018

(65) Prior Publication Data
US 2020/0100776 A1 Apr. 2, 2020

Related U.S. Application Data

(60) Provisional application No. 62/456,940, filed on Feb. 9, 2017.

(51) Int. Cl.
*A61B 10/02* (2006.01)
*A61B 5/00* (2006.01)
(Continued)

(52) U.S. Cl.
CPC ...... *A61B 10/0233* (2013.01); *A61B 5/02042* (2013.01); *A61B 5/6853* (2013.01);
(Continued)

(58) Field of Classification Search
CPC ............ A61B 10/0233; A61B 5/02042; A61B 5/6853; A61B 10/04; A61B 17/1204;
(Continued)

(56) References Cited

U.S. PATENT DOCUMENTS 5,474,530 A * 12/1995 Passafaro ............. A61B 18/245
601/2
5,569,201 A 10/1996 Burns
(Continued)

FOREIGN PATENT DOCUMENTS

WO WO-2015006607 A1 1/2015

OTHER PUBLICATIONS

International Search Report and Written Opinion for application No. PCT/US2018/017621, Mailed on May 10, 2018, 18 pages.
(Continued)

*Primary Examiner* — Richard G Louis
(74) *Attorney, Agent, or Firm* — Haynes & Boone, LLP.

(57) ABSTRACT

A medical system includes an outer catheter comprising one or more first lumens, a sealing device coupled to the outer catheter, an inner instrument configured to be slideably deployed through one of the one or more first lumens and comprising one or more first sensors configured to detect one or more anatomical features below a surface of the anatomic passageway, one or more second sensors, and a processor. The processor is configured to detect bleeding into the anatomic passageway from outside the anatomic passageway using the one or more second sensors and disable advancement of the inner instrument when the one or more first sensors detect the one or more anatomical fea-
(Continued)

tures. The one or more second sensors are configured to be positioned distal to the sealing device and mounted on the inner instrument near a distal end of the inner instrument.

19 Claims, 11 Drawing Sheets

(51) Int. Cl.
*A61B 5/02* (2006.01)
*A61B 10/04* (2006.01)
*A61B 17/12* (2006.01)
*A61B 18/14* (2006.01)
*A61B 34/20* (2016.01)
*A61B 1/267* (2006.01)
*A61B 17/00* (2006.01)
*A61B 18/00* (2006.01)
*A61B 90/00* (2016.01)

(52) U.S. Cl.
CPC .......... *A61B 10/04* (2013.01); *A61B 17/1204* (2013.01); *A61B 17/12136* (2013.01); *A61B 18/1492* (2013.01); *A61B 34/20* (2016.02); *A61B 1/267* (2013.01); *A61B 2017/00022* (2013.01); *A61B 2017/00119* (2013.01); *A61B 2017/0034* (2013.01); *A61B 2017/00809* (2013.01); *A61B 2018/00577* (2013.01); *A61B 2034/2051* (2016.02); *A61B 2034/2061* (2016.02); *A61B 2034/2063* (2016.02); *A61B 90/37* (2016.02)

(58) Field of Classification Search
CPC .......... A61B 17/12136; A61B 18/1492; A61B 34/20; A61B 1/267; A61B 90/37; A61B 2017/00022; A61B 2017/00119; A61B 2017/0034; A61B 2017/00809; A61B 2018/00577

See application file for complete search history.

(56) References Cited

U.S. PATENT DOCUMENTS

| | | | | |
|---|---|---|---|---|
| 5,687,739 A * | 11/1997 | McPherson | ........ | A61B 10/0266 600/567 |
| 5,728,133 A * | 3/1998 | Kontos | .............. | A61B 17/0057 606/1 |
| 5,993,389 A * | 11/1999 | Driscoll, Jr. | ........... | A61B 8/445 600/371 |
| 9,993,306 B2 | 6/2018 | Keast et al. | | |
| 2002/0165574 A1 * | 11/2002 | Ressemann | ...... | A61B 17/12045 604/509 |
| 2002/0183620 A1 * | 12/2002 | Tearney | ............... | A61B 5/6853 600/431 |
| 2004/0097805 A1 * | 5/2004 | Verard | .................. | A61B 34/20 600/428 |
| 2004/0215312 A1 * | 10/2004 | Andreas | .................. | A61F 2/958 623/1.11 |
| 2005/0154277 A1 * | 7/2005 | Tang | .................. | A61B 1/00156 600/407 |
| 2005/0272975 A1 * | 12/2005 | McWeeney | ....... | A61M 25/0068 600/172 |
| 2006/0095066 A1 * | 5/2006 | Chang | .................. | A61M 25/10 606/199 |
| 2007/0255304 A1 | 11/2007 | Roschak et al. | | |
| 2010/0174170 A1 * | 7/2010 | Razavi | .............. | A61M 25/0662 600/371 |
| 2010/0222647 A1 * | 9/2010 | Hashimshony | .......... | A61B 1/04 600/301 |
| 2011/0082370 A1 * | 4/2011 | Ducharme | ....... | A61B 17/00234 600/249 |
| 2011/0196376 A1 * | 8/2011 | Ozgur | ................ | A61B 17/1703 606/80 |
| 2012/0022562 A1 | 1/2012 | Willard | | |
| 2013/0030363 A1 * | 1/2013 | Wong | ..................... | A61B 34/20 604/95.04 |
| 2013/0304107 A1 | 11/2013 | Hassan et al. | | |
| 2014/0088457 A1 * | 3/2014 | Johnson | .................. | A61B 10/04 606/192 |
| 2014/0236207 A1 | 8/2014 | Makower et al. | | |
| 2015/0011856 A1 * | 1/2015 | Arevalos | .............. | A61B 5/0538 600/371 |
| 2017/0007310 A1 * | 1/2017 | Rajagopalan | ........ | A61B 5/0084 |
| 2019/0307511 A1 * | 10/2019 | Ludwin | .................. | A61B 5/068 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

International Preliminary Report on Patentability for Application No. PCT/US2018/017621, mailed on Aug. 22, 2019, 10 pages.

\* cited by examiner

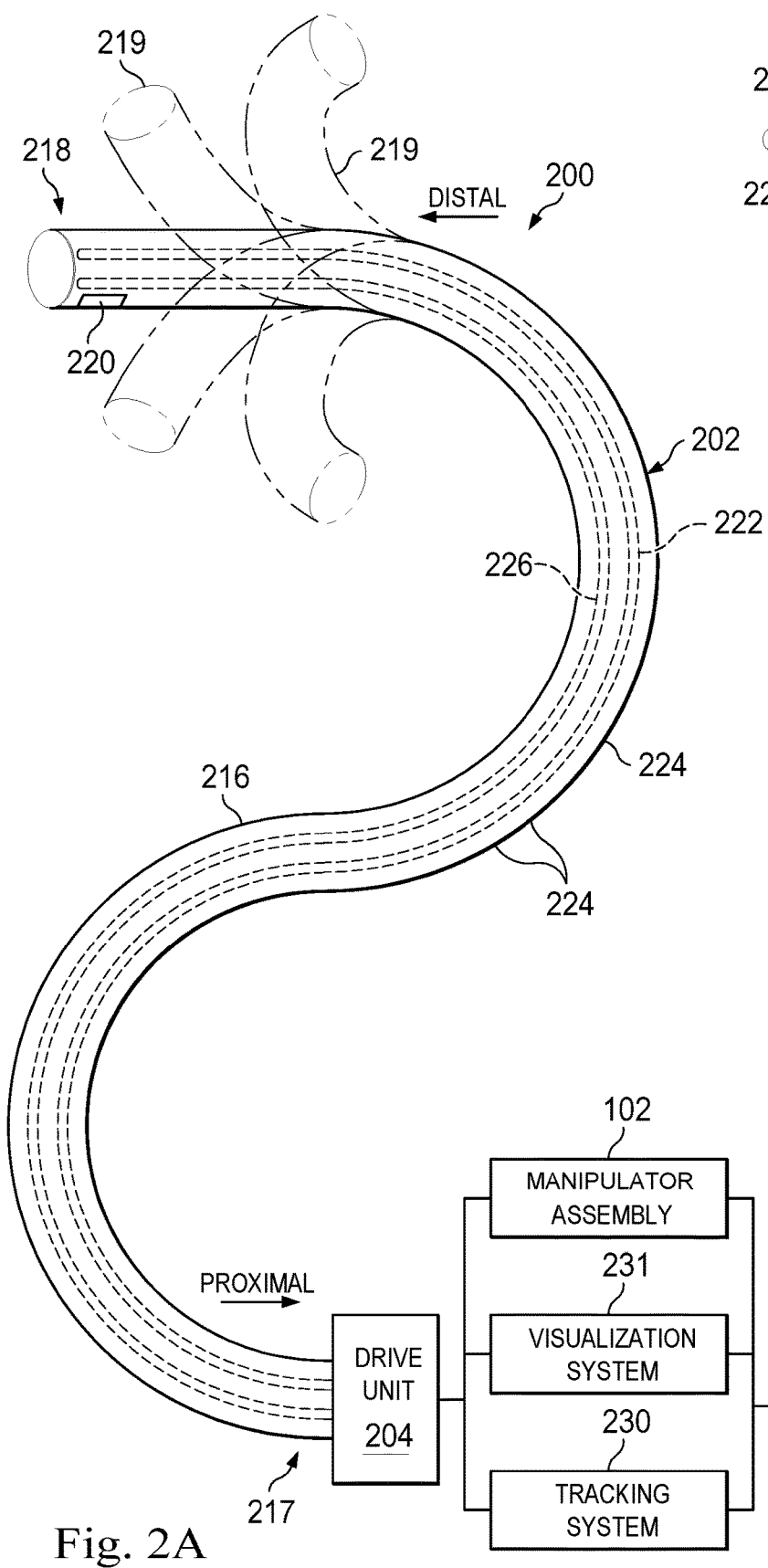

SYSTEMS AND METHODS OF ACCESSING ENCAPSULATED TARGETS

RELATED APPLICATIONS

This patent application is a U.S. National Stage patent application of International Patent Application No. PCT/US2018/017621 filed on Feb. 9, 2018, the benefit of which is claimed, and claims priority to and benefit of the filing date of U.S. Provisional Patent Application No. 62/456,940, entitled "Systems and Methods of Accessing Encapsulated Targets," filed Feb. 9, 2017, each of which is incorporated by reference herein in its entirety.

FIELD

The present disclosure is directed to systems and methods for performing minimally invasive procedures to access encapsulated targets within tissue.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions clinicians may insert minimally invasive medical instruments (including surgical, diagnostic, therapeutic, or biopsy instruments) to reach a target tissue location. One such minimally invasive technique is to use a flexible and/or steerable elongate device, such as a flexible catheter, that is inserted into anatomic passageways and navigated toward a region of interest within the patient anatomy. Given the small size of some of the anatomic passageways or the encapsulation of target tissue within the anatomy surrounding the anatomic passageways, it isn't always possible to navigate the elongate device all the way to the target tissue using just the anatomic passageways.

Accordingly, it would be advantageous to provide devices and techniques to safely access target tissue that is encapsulated within the tissue surrounding anatomic passageways.

SUMMARY

The embodiments of the invention are best summarized by the claims that follow the description.

Consistent with some embodiments, a medical system for performing a minimally invasive procedure within anatomic passageways includes an outer catheter including one or more first lumens, a sealing device coupled to the outer catheter, an inner instrument configured to be slideably deployed through one of the one or more first lumens, and one or more first sensors for detecting bleeding wherein the one or more first sensors are configured to be positioned distal to the sealing device.

Consistent with some embodiments, a non-transitory machine-readable medium includes a plurality of machine-readable instructions which when executed by one or more processors associated with a medical device are adapted to cause the one or more processors to perform a method. The method includes detecting bleeding within one or more passageways of a patient anatomy using one or more first sensors positioned on a medical instrument and activating a sealing device to seal the one or more passageways from the bleeding. The one or more first sensors are positioned distal to the sealing device. The medical instrument includes an outer catheter and an inner instrument configured to be slideably deployed through a lumen of the outer catheter. The inner instrument is further configured to penetrate a surface of the one or more passageways at a point of entry Consistent with some embodiments, a method of performing a procedure on target anatomical tissue includes traversing an outer catheter through anatomic passageways of a patient, the outer catheter comprising one or more first lumens, positioning a distal end of the outer catheter toward a point of entry using guidance from a tracking system, deploying an inner instrument through one of the one or more first lumens, and positioning the inner instrument at the point of entry. The inner instrument includes one or more second lumens. The method further includes deploying a working instrument through one of the one or more second lumens and towards the target anatomical tissue through the point of entry, inserting the inner instrument through the point of entry and towards the target anatomical tissue, replacing the working instrument with a medical instrument, and performing a medical procedure. The point of entry is on a surface of the anatomic passageways.

Consistent with some embodiments, a medical system for performing a medical procedure on an anatomical target within one or more anatomic passageways includes a steerable outer catheter having one or more first lumens, an inner instrument having one or more second lumens, and a working instrument configured to be slideably deployed through the one or more second lumens of the inner instrument. The inner instrument is configured to be slideably deployed through one of the one or more first lumens of the outer catheter. The working instrument includes a distal end for penetrating a surface of the one or more anatomic passageways. The inner instrument acts as a dilation device for delivery of the working instrument to the anatomical target.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

FIGS. 2A and 2B are simplified diagrams of a medical instrument system according to some embodiments.

Figure 1:
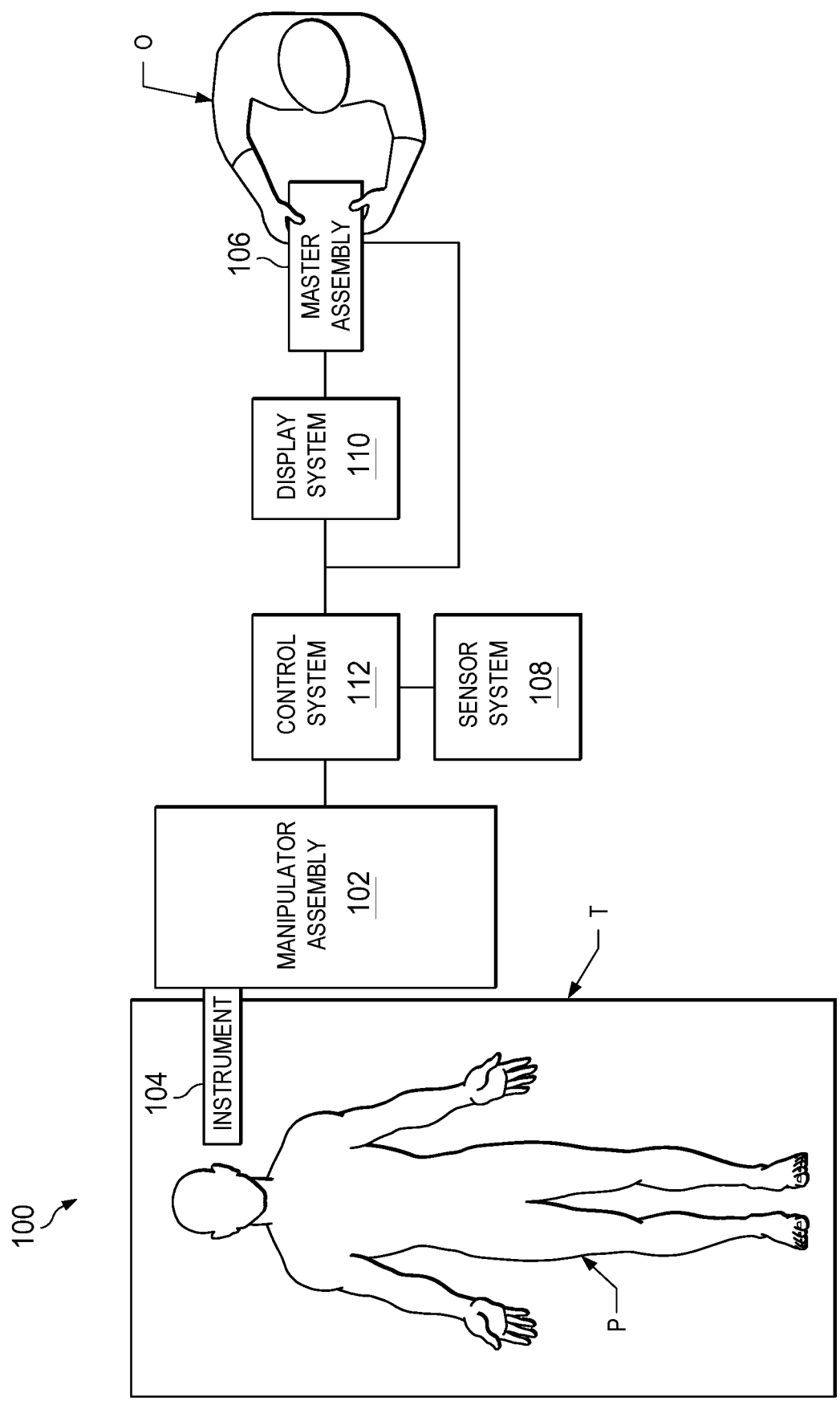
FIG. 1 is a simplified diagram of a teleoperated medical system according to some embodiments.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Various lung bronchoscopic procedures involve navigating an elongate device, such as a flexible catheter, to within proximity of target tissue, such as a lesion or tumor, within the lungs under endoscopic guidance. Once near the target lesion, a procedure can be performed such as a biopsy where a biopsy needle can be delivered within a lumen of the elongate device to obtain a sample of the lesion tissue which is analyzed to, for example, determine whether it is cancerous or non-cancerous. While rough guidance to the target anatomy is performed with endoscopic visualization and the biopsy is often performed under fluoroscopy, in the case where the lesion is not directly accessible via the bronchial passageways or is otherwise embedded within the parenchymal tissue, it is necessary to penetrate the parenchymal tissue to access the target tissue. This involves navigation of the elongate device to a suitable point of entry where the parenchymal tissue is to be penetrated, penetrating the parenchymal tissue, and then deploying a medical instrument to the target tissue through the parenchymal tissue.

Penetration of the parenchymal tissue to reach the target tissue may also introduce risks that are not generally present during bronchoscopic procedures where parenchymal tissue penetration does not occur. For example, the parenchymal tissue typically includes numerous blood vessels that, if damaged during the bronchoscopic procedure, could result in excessive bleeding into the bronchial passageways, which could compromise breathing function. As another example, the parenchymal tissue is surrounded by pleural tissues that, if damaged, could result in a pneumothorax. Accordingly, it would be advantageous to support bronchoscopic procedures that result in penetration of the parenchymal tissue with one or more sensors systems and/or mitigation devices that can detect blood vessels and/or pleural tissue before they are damaged, reduce the impact of bleeding should it occur, reduce the likelihood of pneumothorax should the pleural tissue be damaged, and/or the like.

This disclosure focuses primarily on embodiments where the passageways being traversed are airways in lungs. However, one of ordinary skill in the art would understand that these disclosures are equally applicable to other types of passageways that include one or more branch points. For example, other suitable anatomic passageways include vasculature, renal calyces, lymphatic vessels, and/or the like. In other examples, the passageways may correspond to non-anatomic passageways including sewer tunnels, plumbing pipes, conduits, heating ventilation and air conditioning (HVAC) ducts, mines, caves, and/or the like where the penetration of passageway walls and the controlling of leaks is desirable.

FIG. 1 is a simplified diagram of a teleoperated medical system 100 according to some embodiments. In some embodiments, teleoperated medical system 100 may be suitable for use in, for example, medical, surgical, diagnostic, therapeutic, or biopsy procedures. In some examples, teleoperated medical system may operate in a non-teleoperational manner under non-teleoperator control. As shown in FIG. 1, medical system 100 generally includes a manipulator assembly 102 for operating a medical instrument 104 in performing various procedures on a patient P. Manipulator assembly 102 is mounted to or near an operating table T. A master assembly 106 allows an operator O (e.g., a surgeon, a clinician, or a physician as illustrated in FIG. 1) to view the interventional site and to control manipulator assembly 102.

Master assembly 106 may be located at an operator's console which is usually located in the same room as operating table T, such as at the side of a surgical table on which patient P is located. However, it should be understood that operator O can be located in a different room or a completely different building from patient P. Master assembly 106 generally includes one or more control devices for controlling manipulator assembly 102. The control devices may include any number of a variety of input devices, such as joysticks, trackballs, data gloves, trigger-guns, hand-operated controllers, voice recognition devices, body motion or presence sensors, and/or the like. To provide operator O a strong sense of directly controlling instruments 104 the control devices may be provided with the same degrees of freedom as the associated medical instrument 104. In this manner, the control devices provide operator O with telepresence or the perception that the control devices are integral with medical instruments 104.

In some embodiments, the control devices may have more or fewer degrees of freedom than the associated medical instrument 104 and still provide operator O with telepresence. In some embodiments, the control devices may optionally be manual input devices which move with six degrees of freedom, and which may also include an actuatable handle for actuating instruments (for example, for closing grasping jaws, applying an electrical potential to an electrode, delivering a medicinal treatment, and/or the like).

Manipulator assembly 102 supports medical instrument 104 and may include a kinematic structure of one or more non-servo controlled links (e.g., one or more links that may be manually positioned and locked in place, generally referred to as a set-up structure), a teleoperated kinematic structure, and/or a teleoperational manipulator. Manipulator assembly 102 may optionally include a plurality of actuators or motors that drive inputs on medical instrument 104 in response to commands from the control system (e.g., a control system 112). The actuators may optionally include drive systems that when coupled to medical instrument 104 may advance medical instrument 104 into a naturally or surgically created anatomic orifice. Other drive systems may move the distal end of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like. Actuator position sensors such as resolvers, encoders, potentiometers, and other mechanisms may provide sensor data to medical system 100 describing the rotation and orientation of the motor shafts. This position sensor data may be used to determine motion of the objects manipulated by the actuators.

Teleoperated medical system 100 may include a sensor system 108 with one or more sub-systems for receiving information about the instruments of manipulator assembly 102. Such sub-systems may include a position/location sensor system (e.g., an electromagnetic (EM) sensor system); a shape sensor system for determining the position, orientation, speed, velocity, pose, and/or shape of a distal end and/or of one or more segments along a flexible body that may make up medical instrument 104; and/or a visualization system for capturing images from the distal end of medical instrument 104.

Teleoperated medical system 100 also includes a display system 110 for displaying an image or representation of the surgical site and medical instrument 104 generated by subsystems of sensor system 108. Display system 110 and master assembly 106 may be oriented so operator O can control medical instrument 104 and master assembly 106 with the perception of telepresence.

In some embodiments, medical instrument 104 may have a visualization system (discussed in more detail below), which may include a viewing scope assembly that records a concurrent or real-time image of a surgical site and provides the image to the operator O through one or more displays of medical system 100, such as one or more displays of display system 110. The concurrent image may be, for example, a two or three dimensional image captured by an endoscope positioned within the surgical site. In some embodiments, the visualization system includes endoscopic components that may be integrally or removably coupled to medical instrument 104. However in some embodiments, a separate endoscope, attached to a separate manipulator assembly may be used with medical instrument 104 to image the surgical site. The visualization system may be implemented as hardware, firmware, software or a combination thereof which interact with or are otherwise executed by one or more computer processors, which may include the processors of a control system 112.

Display system 110 may also display an image of the surgical site and medical instruments captured by the visualization system. In some examples, teleoperated medical system 100 may configure medical instrument 104 and controls of master assembly 106 such that the relative positions of the medical instruments are similar to the relative positions of the eyes and hands of operator O. In this manner operator O can manipulate medical instrument 104 and the hand control as if viewing the workspace in substantially true presence. By true presence, it is meant that the presentation of an image is a true perspective image simulating the viewpoint of an operator that is physically manipulating medical instrument 104.

In some examples, display system 110 may present images of a surgical site recorded pre-operatively or intraoperatively using image data from imaging technology such as, computed tomography (CT), magnetic resonance imaging (MM), fluoroscopy, thermography, ultrasound, optical coherence tomography (OCT), thermal imaging, impedance imaging, laser imaging, nanotube X-ray imaging, and/or the like. The pre-operative or intra-operative image data may be presented as two-dimensional, three-dimensional, or four-dimensional (including e.g., time based or velocity based information) images and/or as images from models created from the pre-operative or intra-operative image data sets.

In some embodiments, often for purposes of imaged guided surgical procedures, display system 110 may display a virtual navigational image in which the actual location of medical instrument 104 is registered (i.e., dynamically referenced) with the preoperative or concurrent images/model. This may be done to present the operator O with a virtual image of the internal surgical site from a viewpoint of medical instrument 104. In some examples, the viewpoint may be from a tip of medical instrument 104. An image of the tip of medical instrument 104 and/or other graphical or alphanumeric indicators may be superimposed on the virtual image to assist operator O controlling medical instrument 104. In some examples, medical instrument 104 may not be visible in the virtual image.

In some embodiments, display system 110 may display a virtual navigational image in which the actual location of medical instrument 104 is registered with preoperative or concurrent images to present the operator O with a virtual image of medical instrument 104 within the surgical site from an external viewpoint. An image of a portion of medical instrument 104 or other graphical or alphanumeric indicators may be superimposed on the virtual image to assist operator O in the control of medical instrument 104. As described herein, visual representations of data points may be rendered to display system 110. For example, measured data points, moved data points, registered data points, and other data points described herein may be displayed on display system 110 in a visual representation. The data points may be visually represented in a user interface by a plurality of points or dots on display system 110 or as a rendered model, such as a mesh or wire model created based on the set of data points. In some examples, the data points may be color coded according to the data they represent. In some embodiments, a visual representation may be refreshed in display system 110 after each processing operation has been implemented to alter data points.

Teleoperated medical system 100 may also include control system 112. Control system 112 includes at least one memory and at least one computer processor (not shown) for effecting control between medical instrument 104, master assembly 106, sensor system 108, and display system 110. Control system 112 also includes programmed instructions (e.g., a non-transitory machine-readable medium storing the instructions) to implement some or all of the methods described in accordance with aspects disclosed herein, including instructions for providing information to display system 110. While control system 112 is shown as a single block in the simplified schematic of FIG. 1, the system may include two or more data processing circuits with one portion of the processing optionally being performed on or adjacent to manipulator assembly 102, another portion of the processing being performed at master assembly 106, and/or the like. The processors of control system 112 may execute instructions comprising instruction corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may receive force and/or torque feedback from medical instrument 104. Responsive to the feedback, control system 112 may transmit signals to master assembly 106. In some examples, control system 112 may transmit signals instructing one or more actuators of manipulator assembly 102 to move medical instrument 104. Medical instrument 104 may extend into an internal surgical site within the body of patient P via openings in the body of patient P. Any suitable conventional and/or specialized actuators may be used. In some examples, the one or more actuators may be separate from, or integrated with, manipulator assembly 102. In some embodiments, the one or more actuators and manipulator assembly 102 are provided as part of a teleoperational cart positioned adjacent to patient P and operating table T.

Control system 112 may optionally further include a virtual visualization system to provide navigation assistance to operator O when controlling medical instrument 104 during an image-guided surgical procedure. Virtual navigation using the virtual visualization system may be based upon reference to an acquired preoperative or intraoperative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. Software, which may be used in combination with manual inputs, is used to convert the recorded images into segmented two dimensional or three dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intra-operatively during a clinical procedure. In some embodiments, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, sensor system 108 may be used to compute an approximate location of medical instrument 104 with respect to the anatomy of patient P. The location can be used to produce both macro-level (external) tracking images of the anatomy of patient P and virtual internal images of the anatomy of patient P. The system may implement one or more electromagnetic (EM) sensor, fiber optic sensors, and/or other sensors to register and display a medical implement together with preoperatively recorded surgical images, such as those from a virtual visualization system, are known. For example International Patent Application Publication No. WO 2016/191298 (published Dec. 1, 2016) (disclosing "Systems and Methods of Registration for Image Guided Surgery") which is incorporated by reference herein in its entirety, discloses one such system. Teleoperated medical system 100 may further include optional operations and support systems (not shown) such as illumination systems, steering control systems, irrigation systems, and/or suction systems. In some embodiments, teleoperated medical system 100 may include more than one teleoperational manipulator assembly associated with more than one master assembly, and/or more than one non-teleoperational manipulator assembly. The exact number of teleoperational and/or non-teleoperational manipulator assemblies will depend on the surgical procedure and the space constraints within the operating room, among other factors. Master assembly 106 may be collocated or they may be positioned in separate locations. Multiple master assemblies allow more than one operator to control one or more teleoperational manipulator assemblies in various combinations.

FIG. 2A is a simplified diagram of a medical instrument system 200 according to some embodiments. In some embodiments, medical instrument system 200 may be used as medical instrument 104 in an image-guided medical procedure performed with teleoperated medical system 100. In some examples, medical instrument system 200 may be used for non-teleoperational exploratory procedures or in procedures involving traditional manually operated medical instruments, such as endoscopy. Optionally medical instrument system 200 may be used to gather (i.e., measure) a set of data points corresponding to locations within anatomic passageways of a patient, such as patient P.

Medical instrument system 200 includes elongate device 202, such as a flexible catheter, coupled to a drive unit 204. Elongate device 202 includes a flexible body 216 having proximal end 217 and distal end or tip portion 218. In some embodiments, flexible body 216 has an approximately 3 mm outer diameter. Other flexible body outer diameters may be larger or smaller.

Medical instrument system 200 further includes a tracking system 230 for determining the position, orientation, speed, velocity, pose, and/or shape of distal end 218 and/or of one or more segments 224 along flexible body 216 using one or more sensors and/or imaging devices as described in further detail below. The entire length of flexible body 216, between distal end 218 and proximal end 217, may be effectively divided into segments 224. If medical instrument system 200 is consistent with medical instrument 104 of a teleoperated medical system 100, tracking system 230. Tracking system 230 may optionally be implemented as hardware, firmware, software or a combination thereof which interact with or are otherwise executed by one or more computer processors, which may include the processors of control system 112 in FIG. 1.

Tracking system 230 may optionally track distal end 218 and/or one or more of the segments 224 using a shape sensor 222. Shape sensor 222 may optionally include an optical fiber aligned with flexible body 216 (e.g., provided within an interior channel (not shown) or mounted externally). In one embodiment, the optical fiber has a diameter of approximately 200 μm. In other embodiments, the dimensions may be larger or smaller. The optical fiber of shape sensor 222 forms a fiber optic bend sensor for determining the shape of flexible body 216. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in some embodiments may employ other suitable strain sensing techniques, such as Rayleigh scattering, Raman scattering, Brillouin scattering, and Fluorescence scattering. In some embodiments, the shape of the elongate device may be determined using other techniques. For example, a history of the distal end pose of flexible body 216 can be used to reconstruct the shape of flexible body 216 over the interval of time. In some embodiments, tracking system 230 may optionally and/or additionally track distal end 218 using a position sensor system 220. Position sensor system 220 may be a component of an EM sensor system with positional sensor system 220 including one or more conductive coils that may be subjected to an externally generated electromagnetic field. Each coil of EM sensor system 220 then produces an induced electrical signal having characteristics that depend on the position and orientation of the coil relative to the externally generated electromagnetic field. In some embodiments, position sensor system 220 may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety. Alternatively, position sensor system 220 may include other types of localization sensors including impedance based sensors, ultrasound sensors, time of flight based sensors, and/or the like.

In some embodiments, tracking system 230 may alternately and/or additionally rely on historical pose, position, or orientation data stored for a known point of an instrument system along a cycle of alternating motion, such as breathing. This stored data may be used to develop shape information about flexible body 216. In some examples, a series of positional sensors (not shown), such as electromagnetic (EM) sensors similar to the sensors in position sensor 220 may be positioned along flexible body 216 and then used for shape sensing. In some examples, a history of data from one or more of these sensors taken during a procedure may be used to represent the shape of elongate device 202, particularly if an anatomic passageway is generally static.

Flexible body 216 includes a channel 221 sized and shaped to receive a medical instrument 226. FIG. 2B is a simplified diagram of flexible body 216 with medical instrument 226 extended according to some embodiments. In some embodiments, medical instrument 226 may be used for procedures such as surgery, biopsy, ablation, illumination, irrigation, or suction. Medical instrument 226 can be deployed through channel 221 of flexible body 216 and used at a target location within the anatomy. Medical instrument 226 may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. In various embodiments, medical instrument 226 is a biopsy instrument, which may be used to remove sample tissue or a sampling of cells from a target anatomic location. Medical instrument 226 may further be used in conjunction with one or more sensors to support a desired procedure. The one or more sensors may include sensors to aid in the location of target tissue, avoid contact with or damage to tissue to be avoided, detect undesirable bleeding, and/or the like. The one or more sensors may include one or more Doppler devices, such as Doppler OCT or Doppler ultrasound, monoscopic or stereoscopic imaging sensors, such as a fiber optic bundle, a fiberscope, an endoscope, an optical coherence tomography (OCT) device, ultrasound transducers, and/or the like. The one or more imaging sensors may include one or more cables or optical fibers coupling the one or more imaging sensors to visualization system 231. The one or more imaging sensors may be single or multi-spectral, for example capturing image data in one or more of the visible, infrared, and/or ultraviolet spectrums using techniques such as Fourier transform spectroscopy, Raman Spectroscopy, and/or the like. Alternatively, medical instrument 226 may itself be an image capture probe to which the one or more imaging sensors are mounted. Medical instrument 226 may be advanced from the opening of channel 221 to perform the procedure and then retracted back into the channel when the procedure is complete. Medical instrument 226 may be removed from proximal end 217 of flexible body 216 or from another optional instrument port (not shown) along flexible body 216.

Medical instrument 226 may additionally house cables, linkages, or other actuation controls (not shown) that extend between its proximal and distal ends to controllably the bend distal end of medical instrument 226. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

Flexible body 216 may also house cables, linkages, or other steering controls (not shown) that extend between drive unit 204 and distal end 218 to controllably bend distal end 218 as shown, for example, by broken dashed line depictions 219 of distal end 218. In some examples, at least four cables are used to provide independent "up-down" steering to control a pitch of distal end 218 and "left-right" steering to control a yaw of distal end 281. Steerable elongate devices are described in detail in U.S. patent application Ser. No. 13/274,208 (filed Oct. 14, 2011) (disclosing "Catheter with Removable Vision Probe"), which is incorporated by reference herein in its entirety. In embodiments in which medical instrument system 200 is actuated by a teleoperational assembly, drive unit 204 may include drive inputs that removably couple to and receive power from drive elements, such as actuators, of the teleoperational assembly. In some embodiments, medical instrument system 200 may include gripping features, manual actuators, or other components for manually controlling the motion of medical instrument system 200. Elongate device 202 may be steerable or, alternatively, the system may be non-steerable with no integrated mechanism for operator control of the bending of distal end 218. In some examples, one or more lumens, through which medical instruments can be deployed and used at a target surgical location, are defined in the walls of flexible body 216.

In some embodiments, medical instrument system 200 may include a flexible bronchial instrument, such as a bronchoscope or bronchial catheter, for use in examination, diagnosis, biopsy, or treatment of a lung. Medical instrument system 200 is also suited for navigation and treatment of other tissues, via natural or surgically created connected passageways, in any of a variety of anatomic systems, including the colon, the intestines, the kidneys and kidney calices, the brain, the heart, the circulatory system including vasculature, and/or the like.

The information from tracking system 230 may be sent to a navigation system 232 where it is combined with information from visualization system 231 and/or the preoperatively obtained models to provide the operator with real-time position information. In some examples, the real-time position information may be displayed on display system 110 of FIG. 1 for use in the control of medical instrument system 200. In some examples, control system 116 of FIG. 1 may utilize the position information as feedback for positioning medical instrument system 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In some examples, medical instrument system 200 may be teleoperated within medical system 100 of FIG. 1. In some embodiments, manipulator assembly 102 of FIG. 1 may be replaced by direct operator control. In some examples, the direct operator control may include various handles and operator interfaces for hand-held operation of the instrument.

Figure 3A:
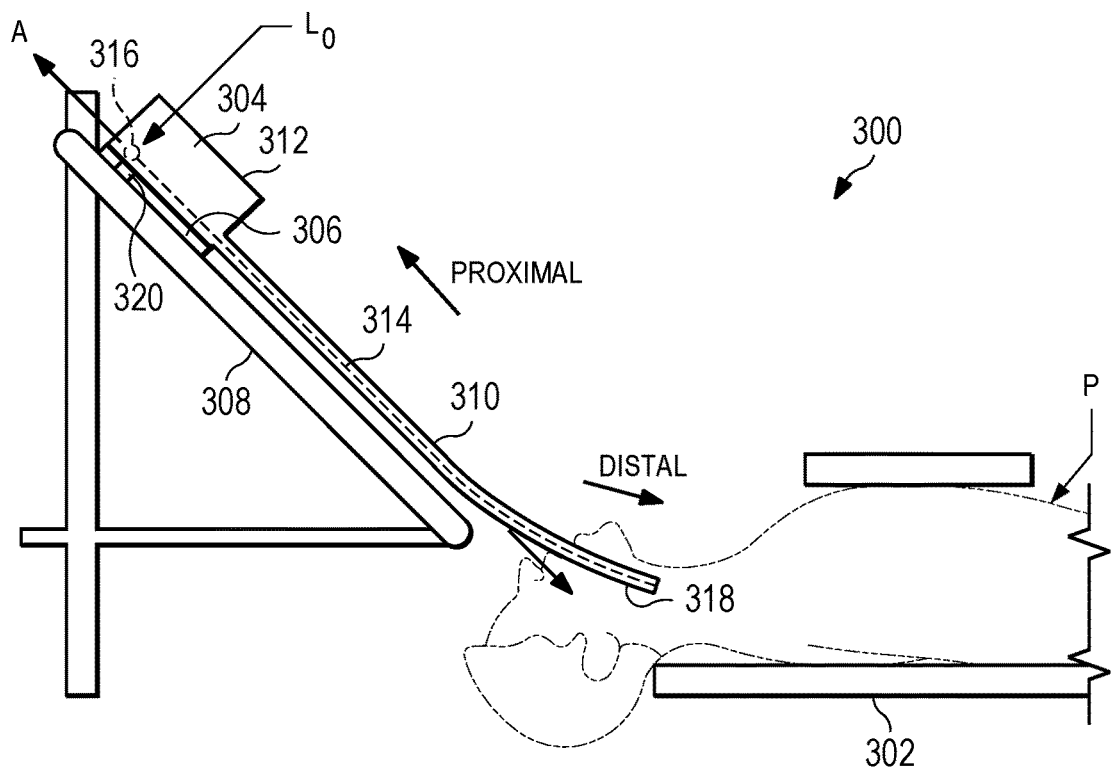
FIGS. 3A and 3B are simplified diagrams of side views of a patient coordinate space including a medical instrument mounted on an insertion assembly according to some embodiments.
Figure 3B:
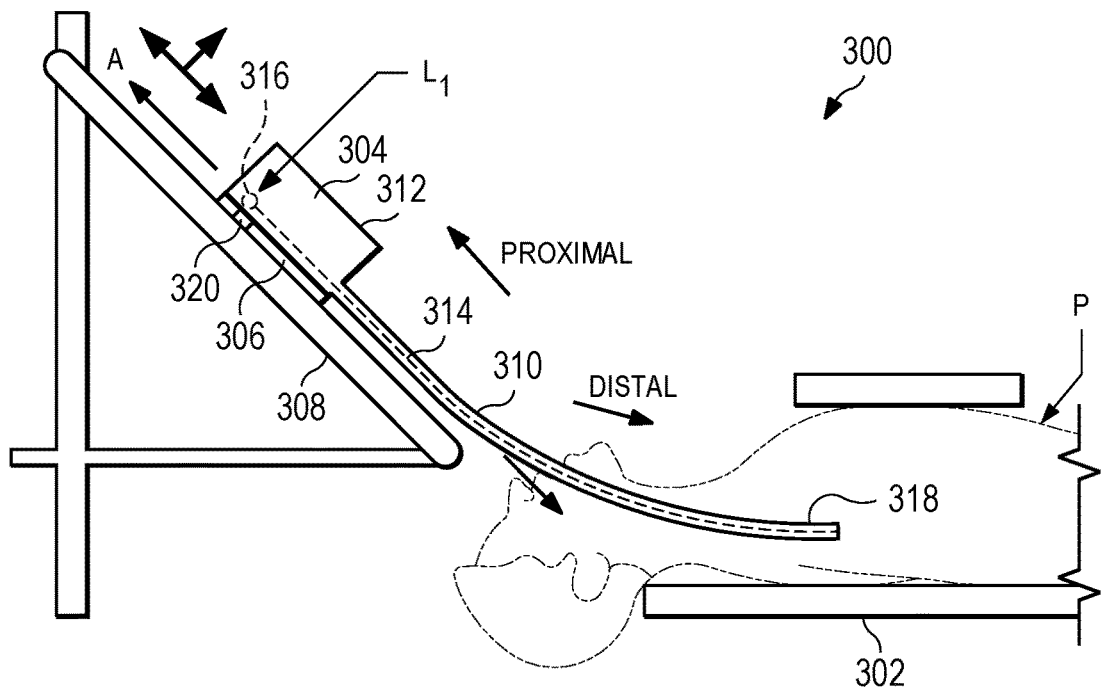

FIGS. 3A and 3B are simplified diagrams of side views of a patient coordinate space including a medical instrument mounted on an insertion assembly according to some embodiments. As shown in FIGS. 3A and 3B, a surgical environment 300 includes a patient P is positioned on platform 302. Patient P may be stationary within the surgical environment in the sense that gross patient movement is limited by sedation, restraint, and/or other means. Cyclic anatomic motion including respiration and cardiac motion of patient P may continue, unless patient is asked to hold his or her breath to temporarily suspend respiratory motion. Accordingly, in some embodiments, data may be gathered at a specific, phase in respiration, and tagged and identified with that phase. In some embodiments, the phase during which data is collected may be inferred from physiological information collected from patient P. Within surgical environment 300, a point gathering instrument 304 is coupled to an instrument carriage 306. In some embodiments, point gathering instrument 304 may use EM sensors, shape-sensors, and/or other sensor modalities. Instrument carriage 306 is mounted to an insertion stage 308 fixed within surgical environment 300. Alternatively, insertion stage 308 may be movable but have a known location (e.g., via a tracking sensor or other tracking device) within surgical environment 300. Instrument carriage 306 may be a component of a manipulator assembly (e.g., manipulator assembly 102) that couples to point gathering instrument 304 to control insertion motion (i.e., motion along the A axis) and, optionally, motion of a distal end 318 of an elongate device 310 in multiple directions including yaw, pitch, and roll. Instrument carriage 306 or insertion stage 308 may include actuators, such as servomotors, (not shown) that control motion of instrument carriage 306 along insertion stage 308.

Elongate device 310 is coupled to an instrument body 312. Instrument body 312 is coupled and fixed relative to instrument carriage 306. In some embodiments, an optical fiber shape sensor 314 is fixed at a proximal point 316 on instrument body 312. In some embodiments, proximal point 316 of optical fiber shape sensor 314 may be movable along with instrument body 312 but the location of proximal point 316 may be known (e.g., via a tracking sensor or other tracking device). Shape sensor 314 measures a shape from proximal point 316 to another point such as distal end 318 of elongate device 310. Point gathering instrument 304 may be substantially similar to medical instrument system 200.

A position measuring device 320 provides information about the position of instrument body 312 as it moves on insertion stage 308 along an insertion axis A. Position measuring device 320 may include resolvers, encoders, potentiometers, and/or other sensors that determine the rotation and/or orientation of the actuators controlling the motion of instrument carriage 306 and consequently the motion of instrument body 312. In some embodiments, insertion stage 308 is linear. In some embodiments, insertion stage 308 may be curved or have a combination of curved and linear sections.

FIG. 3A shows instrument body 312 and instrument carriage 306 in a retracted position along insertion stage 308. In this retracted position, proximal point 316 is at a position $L_0$ on axis A. In this position along insertion stage 308 an A component of the location of proximal point 316 may be set to a zero and/or another reference value to provide a base reference to describe the position of instrument carriage 306, and thus proximal point 316, on insertion stage 308. With this retracted position of instrument body 312 and instrument carriage 306, distal end 318 of elongate device 310 may be positioned just inside an entry orifice of patient P. Also in this position, position measuring device 320 may be set to a zero and/or another reference value (e.g., I=0). In FIG. 3B, instrument body 312 and instrument carriage 306 have advanced along the linear track of insertion stage 308 and distal end 318 of elongate device 310 has advanced into patient P. In this advanced position, the proximal point 316 is at a position $L_1$ on the axis A. In some examples, encoder and/or other position data from one or more actuators controlling movement of instrument carriage 306 along insertion stage 308 and/or one or more position sensors associated with instrument carriage 306 and/or insertion stage 308 is used to determine the position $L_x$ of proximal point 316 relative to position $L_0$. In some examples, position $L_x$ may further be used as an indicator of the distance or insertion depth to which distal end 318 of elongate device 310 is inserted into the passageways of the anatomy of patient P.

Figure 4A:
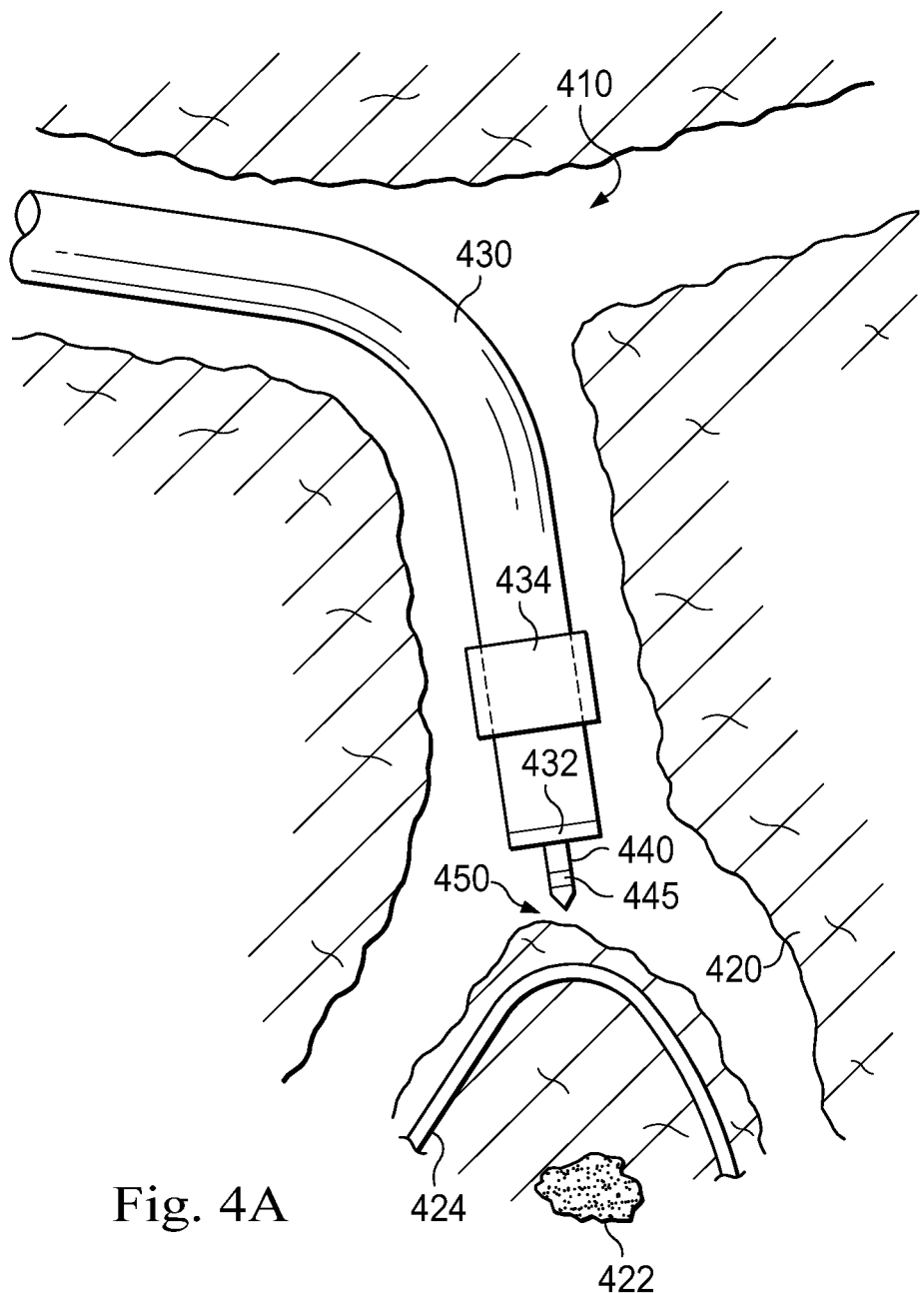
FIG. 4A is a simplified diagram of a side view of medical instruments approaching a point of entry within patient anatomy according to some embodiments.

FIG. 4A is a simplified diagram of a side view of medical instruments approaching a point of entry within patient anatomy according to some embodiments. As shown in FIG. 4A, the patient anatomy includes a plurality of passageways 410 surrounded by tissue 420. In some examples, passageways 410 may correspond to airways or bronchial passageways of a patient's lungs and tissue 420 may correspond to parenchymal tissue of the lungs. In other examples, passageways 410 may correspond to vasculature, colon calices, kidney calices, and/or other anatomic passageways. Located within tissue 420 is target tissue 422 within a region of interest, which may correspond to a lesion, a tumor, and/or the like. Additionally located within tissue 420 is one or more blood vessels 424, which may interfere with access to target tissue 422 during a procedure. As further shown, several medical instruments may be inserted into passageways 410. In some examples, one or more of the medical instruments may be consistent with elongate device 202.

Delivery of the one or medical instruments within passageways 410 to within the vicinity of target tissue 422 can be accomplished using an outer catheter 430 having one or more lumens (not shown). In some examples, outer catheter 430 is consistent with elongate device 202. Outer catheter 430 may be steered so as to position outer catheter 430 where desired within passageways 410. In some examples, a tracking system (such as tracking system 230) may be used in conjunction with one or more position sensors (such as position sensor 220) and/or a shape sensor (such as shape sensor 222) to register outer catheter 430 to one or more pre-operative or intra-operative images and/or models of the patient anatomy and to provide real time localization of outer catheter 430 to help guide the surgeon in steering outer catheter 430. In some examples, an endoscope and/or other imaging device may be inserted into outer catheter 430 through a lumen and may further be used to aid the operator in steering outer catheter 430. In some examples, outer catheter 430 may be steered so that it is in alignment with a point of entry 450 where tissue 420 is to be penetrated. Once in the desired location, outer catheter 430 may optionally be parked.

In some embodiments, outer catheter 430 may include one or more sensors 432 located at or near a distal end of outer catheter 430. The one or more sensors 432 may include one or more Doppler devices, such as Doppler OCT or Doppler ultrasound, one or more imaging sensors, such as a fiber optic bundle, a fiberscope, an endoscope, an OCT device, ultrasound transducers, and/or the like. In some examples, when the one or more sensors 432 are used to aid in the positioning of outer catheter 430 near point of entry 450, the one or more sensors 432 may include a fiberscope, an endoscope, an OCT device, an ultrasound transducer, a Doppler OCT device, a Doppler ultrasound device, and/or the like which may be used to provide live images to the operator as outer catheter 430 is navigated toward point of entry 450. In some examples, when the one or more sensors 432 are used, to aid in avoiding damage to portions of tissue 420 (such as the one or more blood vessels 424), the one or more sensors may include an OCT device, a Doppler OCT device, and/or the like. For example, the Doppler OCT device may be used to detect motion of blood through the one or more blood vessels 424 even when the one or more blood vessels 424 are located below the surface of tissue 420. In some examples, the tissue detection features of the one or more sensors 432 may optionally be used to guide in the steering of outer catheter 430 toward point of entry 450 by providing audio, visual, and/or haptic feedback cues to the operator. In some examples, when the one or more sensors 432 are used to aid in detecting of bleeding, the one or more sensors 432 may include a fiberscope, an endoscope, and/or the like, which may use techniques such as Fourier transform infrared spectroscopy, Raman spectroscopy, and/or the like to aid in the detecting of bleeding.

As further shown in FIG. 4A, outer catheter additionally includes a sealing device 434 located proximal to the one or more sensors 432. Sealing device 434 may include one or more balloons, which may be used to create a seal across one of passageways 410 at a sealing location proximal to point of entry 450. To create the seal at the sealing location, the one or more balloons of sealing device 434 may be expanded and/or enlarged to fill the passageway 410. In some examples, air, saline, and/or some other gas or fluid is injected into the one or more balloons through an inflation lumen (not shown) to expand the one or more balloons until the one or more balloons seal passageway 410 at the sealing location. Creation of the seal by sealing device 434 may be used to isolate portions of passageways 410 proximal to the sealing location from complications introduced by penetrating tissue 420 at point of entry 450. For example, when the penetration of tissue 420 between point of entry 450 and target tissue 422 results in undesirable and/or excessive bleeding (as detected by the one or more sensors 432), sealing device 434 may be used to contain the bleeding to those portions of passageways 410 that are distal to the sealing location. In some examples, inflation of sealing device 434 is manually activated by the operator in response to an observation of bleeding in images captured by the one or more sensors 432 and displayed to the operator, in response to an alarm (visual and/or audio) triggered by automatic detection of the bleeding from information obtained from the one or more sensors 432, and/or automatically in response to the automatic detection of the bleeding. In some examples, the automatic triggering of sealing device 434 may be overridden by the operator. In some embodiments, inflation of sealing device 434 may also occur in response to other conditions, such as the detection that pleural tissue has been penetrated and a risk of pneumothorax is present. In some embodiments, sealing device 434 is a balloon catheter which is slideably deployed through the one or more lumens (not shown) of the outer catheter 430. Although not shown in FIG. 4A, sealing device 434 may optionally be mounted to a sheath that surrounds outer catheter 430.

Outer catheter 430 further includes at least one lumen (not shown) which may be used to deploy an inner instrument 440 to point of entry 450. In some examples, inner instrument 440 is consistent with elongate device 202 and may or may not be steerable. In some examples, inner instrument 440 may also include one or more lumens through which working instruments are deployed to point of entry 450 and/or to areas of tissue 420 between point of entry 450 and target tissue 422. A distal end of inner instrument 440 may include a needle, a blunt dissector, and/or the like, which may be used to penetrate tissue 420 at point of entry 450. The inner instrument 440 may include a biopsy instrument (such as a biopsy needle, biopsy forceps, etc.), an ablation device (such as a cryotherapeutic, RF, microwave, ultrasound, high-intensity focused ultrasound, laser, chemical delivery, or direct heat device), a drug delivery needle, and/or other surgical, diagnostic, or therapeutic tools. Alternatively, when inner instrument 440 is a catheter, the needle, blunt dissector, ablation device, delivery wire, and/or the like may be slideably deployed as one of the working instruments slideably deployed through a lumen of inner instrument 440. In some embodiments, when inner instrument 440 is a catheter, outer catheter may not include sealing device 434. Alternatively, the sealing device 434 may be included on inner instrument 440.

In some embodiments, inner instrument 440 may optionally include one or more sensors 445 located at or near a distal end of inner instrument 440. The one or more sensors 445 may include one or more Doppler devices, such as a Doppler OCT or Doppler ultrasound, one or more imaging sensors, such as an OCT device, ultrasound transducers, and/or the like. In some examples, the one or more sensors 445 are used to aid in the positioning of inner instrument 440 and/or outer catheter 430 near point of entry 450 so as to aid in avoiding damage to portions of tissue 420 (such as the one or more blood vessels 424) before penetration of tissue 420 at point of entry 450 occurs. In some examples, the one or more sensors 445 may include a bleeding detection sensor located proximal to a Doppler or imaging sensor. In some examples, the bleeding detection sensor may be an alternative to or supplement to the bleeding detection features of the one or more sensors 432. In some examples, the tissue detection features of the one or more sensors 432 and/or the one or more sensors 445 may optionally be used to guide the steering of outer catheter 430 toward point of entry 450 by providing audio, visual, and/or haptic feedback cues to the operator. In some examples, the tissue detection features may further be used to automatically prevent further advancement of inner instrument 440 toward point of entry 450 when it is determined that contact with and/or damage to the one or more blood vessels 424 may occur due to further advancement of inner instrument 440. When the one or more sensors 445 include an ultrasound transducer to detect the portions of tissue 420 to avoid, the one or more sensors 445 may additionally be placed in direct contact with tissue 420 at point of entry 450 to improve function of the ultrasound transducer, which often does not provide adequate imaging information when used through air.

Figure 4B:
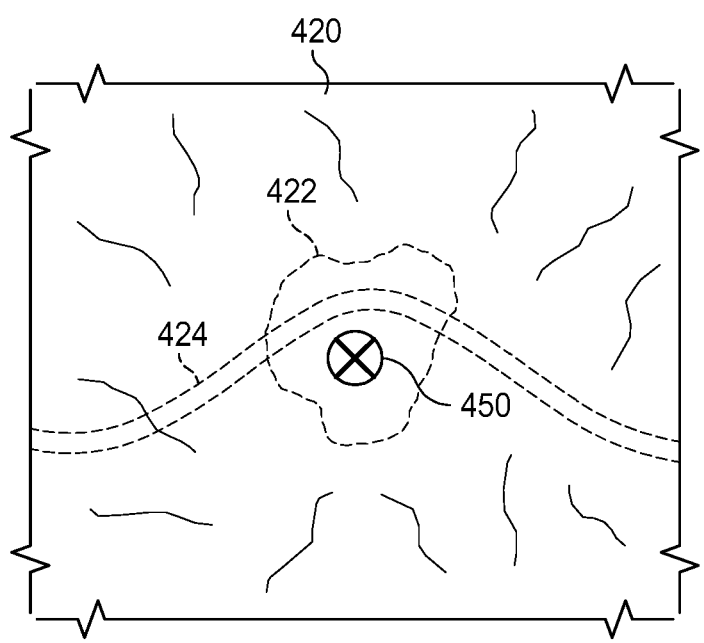
FIG. 4B is a simplified diagram of a distal facing view of a point of entry according to some embodiments.

FIG. 4B is a simplified diagram of a distal or forward facing view of point of entry 450 according to some embodiments. As shown in FIG. 4B, a surface region of tissue 420 is shown with locations of target tissue 422 and the one or more blood vessels 424 below the surface of tissue 420. Also shown is a desired location of point of entry 450. In some examples, images consistent with the example view of FIG. 4B may be captured using the one or more sensors 432 and/or the one or more sensors 445. To reduce the likelihood that the one or more blood vessels 424 are damaged during a procedure, point of entry 450 is selected to provide a path between point of entry 450 and target tissue 422. Although the path is typically straight, when inner instrument 440 is steerable, the path may include one or more bends or curves. Using the tissue detection features of the one or more sensors 432 and/or the one or more sensors 445, the location of the one or more blood vessels 424 is detected and the location of point of entry 450 may be adjusted to avoid contact with and/or damage to the one or more blood vessels 424.

Figure 5:
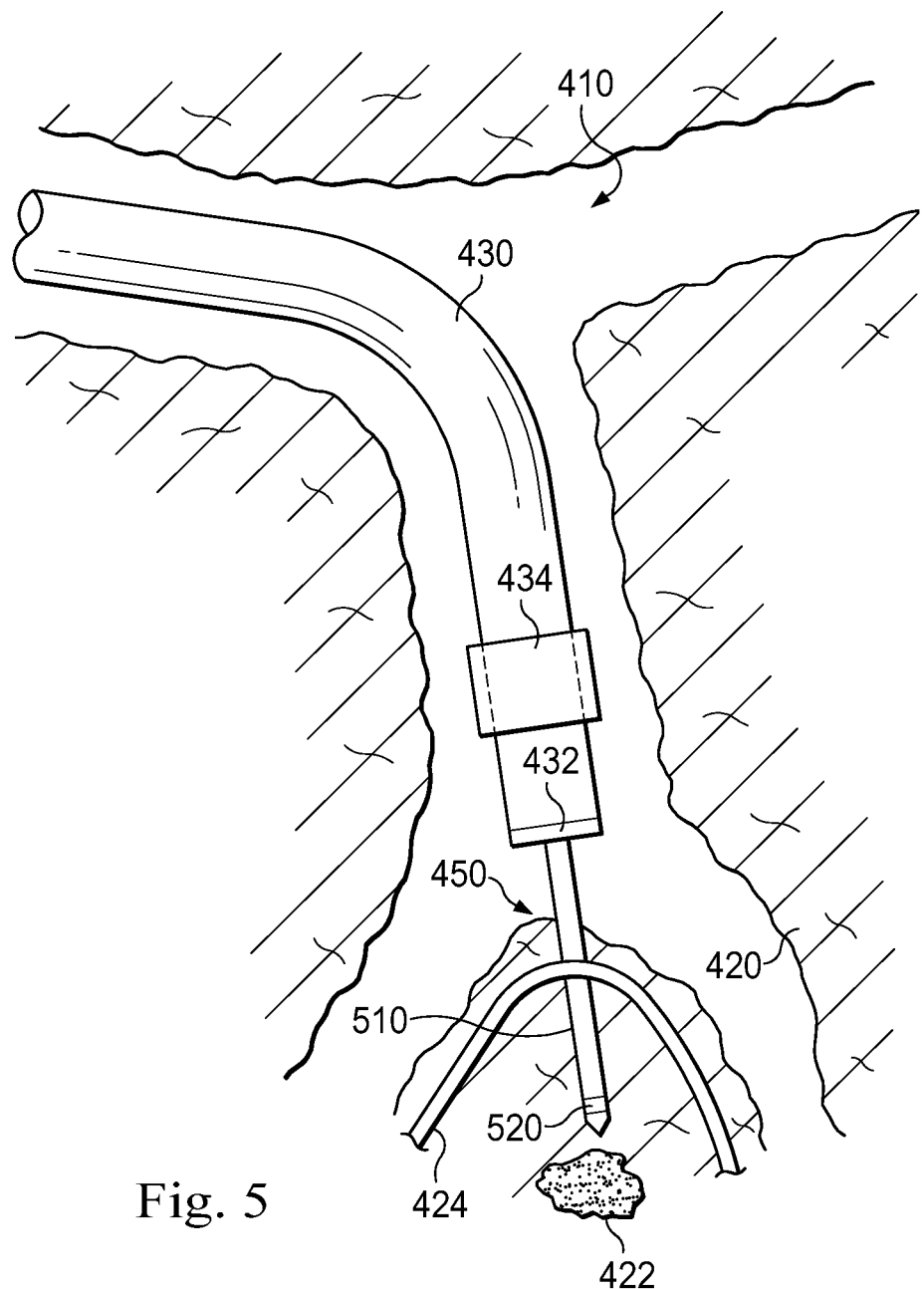
FIG. 5 is a simplified diagram of a side view of medical instruments approaching target tissue within patient anatomy according to some embodiments.

FIG. 5 is a simplified diagram of a side view of medical instruments approaching target tissue 422 according to some embodiments. As shown in FIG. 5, a working instrument 510 is deployed from a lumen (not shown) in outer catheter 430, through point of entry 450 on tissue 420 and is extended toward target tissue 422. In some examples, working instrument 510 is consistent with elongate device 202 and may or may not be steerable and/or is the same as inner instrument 440. In some examples, when inner instrument 440 (not shown) is an inner catheter, working instrument 510 may be representative of any of a number of instruments that may be slideably deployed through one of the lumens (not shown) in inner instrument 440. Inner instrument 440 may include one or more sensors 445 and/or sealing device 434. A distal end of working instrument 510 may include a needle, a blunt dissector, and/or the like, which may be used to further penetrate through tissue 420 between point of entry 450 and target tissue 422. Alternatively, when inner instrument 440 and/or working instrument 510 is a catheter, the needle, blunt dissector, and/or the like may be deployed as one of the instruments slideably deployed through one of the lumens of inner instrument 440 and/or working instrument 510. Once working instrument 510 has reached target tissue 422, working instrument 510 and/or an instrument slideably deployed through one of the lumens of working instrument 510 is replaced by one or more instruments in order to perform a procedure on target tissue 422. In some examples, the one or more instruments may be consistent with medical instrument 226 and may include a biopsy instrument (such as a biopsy needle, biopsy forceps, etc.), an ablation device (such as a cryotherapeutic, RF, microwave, ultrasound, high-intensity focused ultrasound, laser, chemical delivery, or direct heat device), a drug delivery needle, and/or other surgical, diagnostic, or therapeutic tools Working instrument 510 may optionally include one or more sensors 520 located at or near a distal end of working instrument 510. In some examples, the one or more sensors 520 aid in the positioning of the working instrument 510. In some examples, the one or more sensors 520 may include one or more ultrasound transducers, such as forward facing ultrasound transducers, which may be usable to provide one or more images that may help in guiding a distal end of working instrument 510 to target tissue 422 and/or to perform the procedure on target tissue 422. In some embodiments, when working instrument 510 includes a shape sensor (such as shape sensor 222), once working instrument 510 is inserted through point of entry 450, additional knowledge regarding a location of point of entry 450 may be advantageously used to improve the registration of working instrument 510 by placing additional geometric constraints on the positioning data supplied by the shape sensor.

Figure 6:
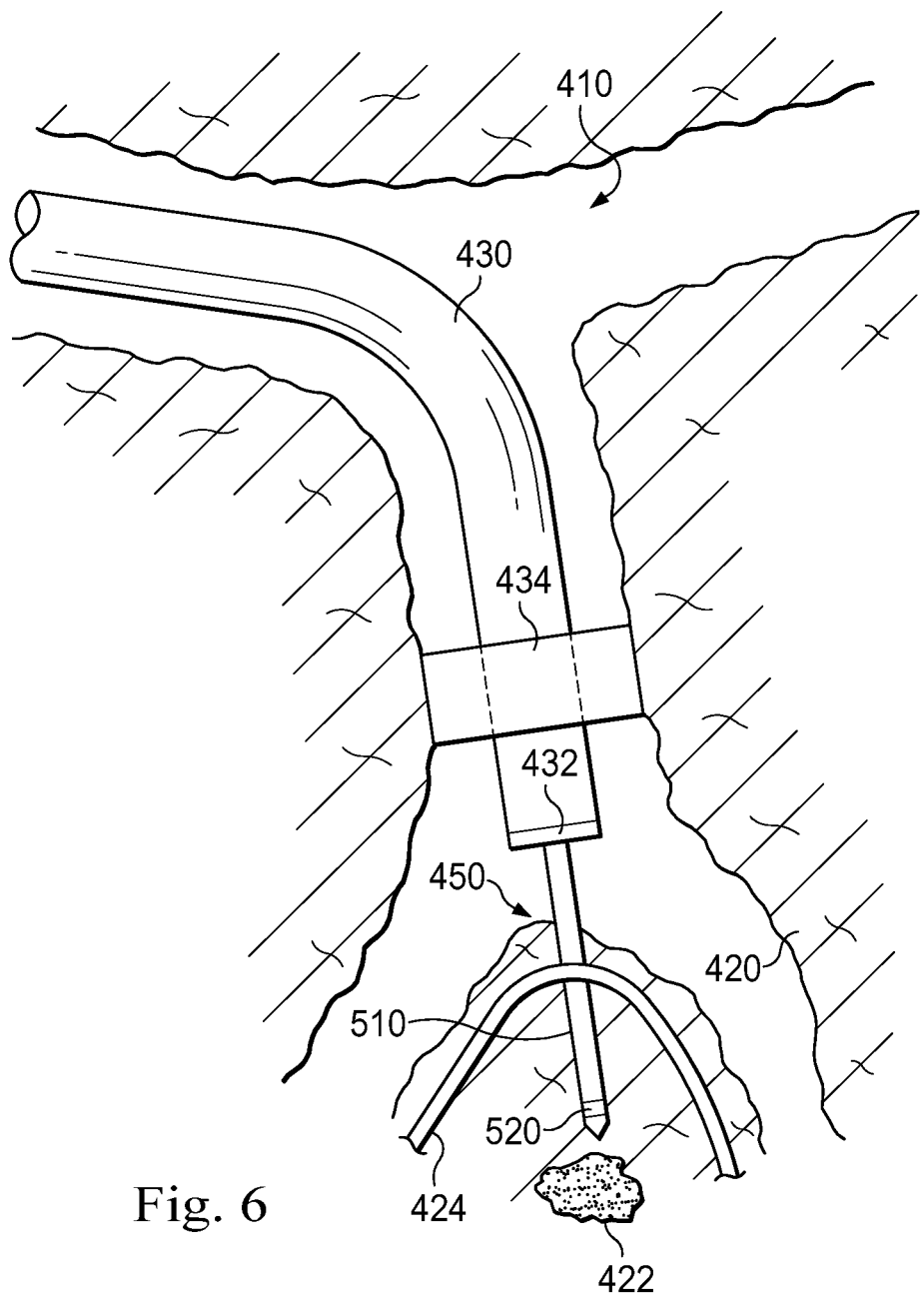
FIG. 6 is a simplified diagram of a side view of medical instruments within patient anatomy with a deployed sealing device according to some embodiments.

FIG. 6 is a simplified diagram of a side view of medical instruments within patient anatomy with deployed sealing device 434 according to some embodiments. As previously discussed, when undesirable and/or excessive bleeding is detected by the one or more sensors 432 and/or damage to the pleural tissue is detected, sealing device 434 may be deployed by inflating the one or more balloons of sealing device 434. As the one or more balloons are inflated, they expand across passageways 410 at the sealing location. In some examples, sealing device 434 may be used to provide a barrier that keeps blood from moving from the distal side of sealing device 434 to the proximal side of sealing device 434 in order control bleeding during the procedure. In some examples, sealing device 434 may also be used to provide a barrier to keep air and/or other gasses or fluids from moving from the proximal side of sealing device 434 to the distal side of sealing device 434 to reduce the likelihood of a pneumothorax.

Figure 7:
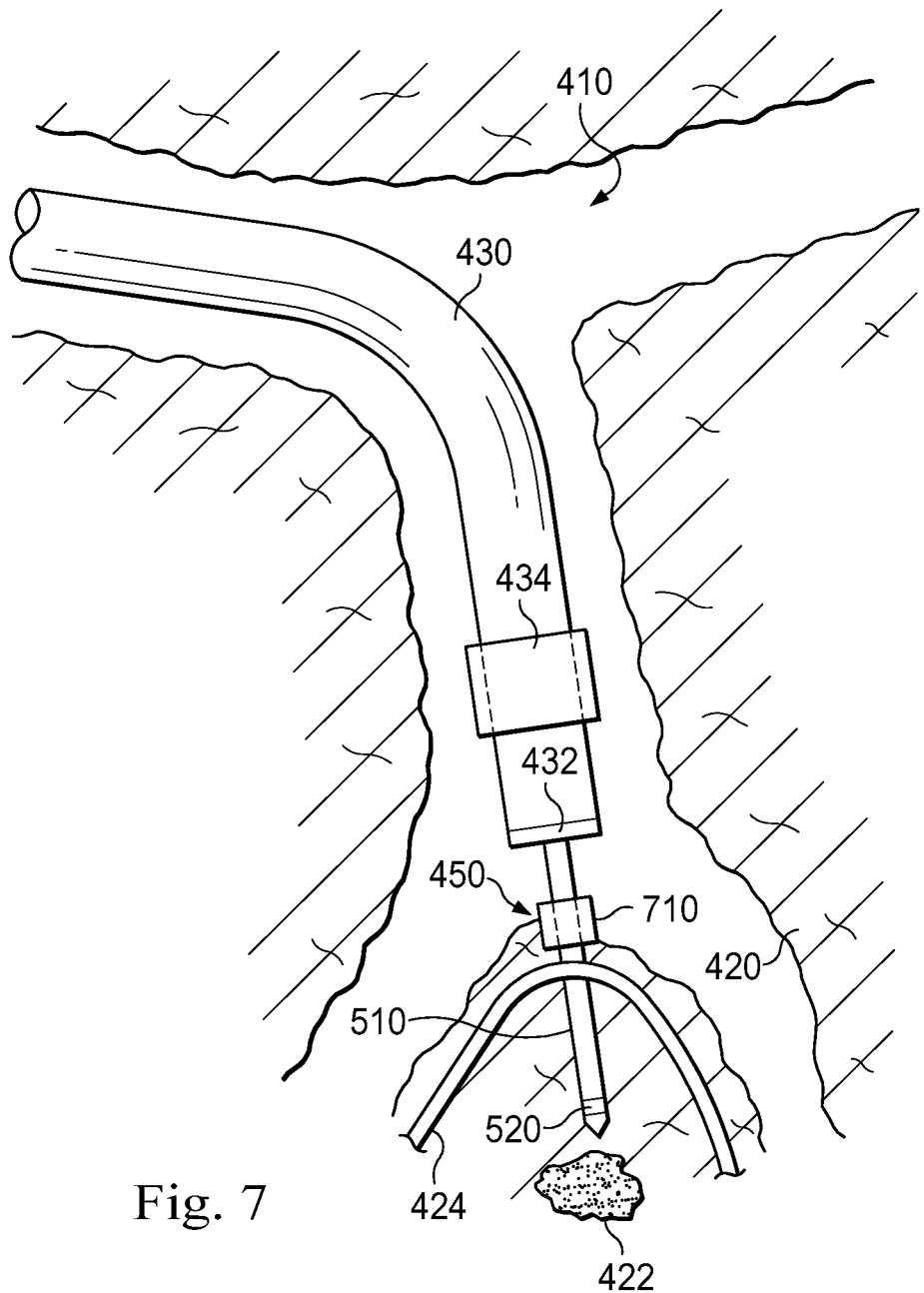
FIG. 7 is a simplified diagram of a side view of medical instruments within patient anatomy with a deployed dilation device according to some embodiments.

FIG. 7 is a simplified diagram of a side view of medical instruments within patient anatomy with a deployed dilation device 710 according to some embodiments. As shown in FIG. 7, working instrument 510 may optionally include dilation device 710 that may be used to enlarge the opening in tissue 420 at point of entry 450 and/or to help keep the opening open while additional instruments 510 are deployed toward target tissue 422. And although dilation device 710 is shown as part of working instrument 510, dilation device 710 could alternatively be mounted to inner instrument 440 when working instrument 510 is deployed through a lumen of inner instrument 440. Like sealing device 434, dilation device 710 may include one or more balloons that may be expanded and/or enlarged to enlarge or help keep open the opening in tissue 420 at point of entry 450. In some examples, air, saline, and/or some other gas or fluid is injected into the one or more balloons through an inflation lumen (not shown) to expand the one or more balloons to a desired level of dilation. Although not shown in FIG. 7, dilation device 710 may optionally be mounted to a sheath that surrounds inner instrument 440 and/or working instrument 510.

As previously described with regards to working instrument 510, working instrument 510 is consistent with elongate device 202 and may or may not be steerable. A distal end of working instrument 510 may include a needle, a blunt dissector, and/or the like, which may be used to further penetrate through tissue 420 between point of entry 450 and target tissue 422. Alternatively, when working instrument 510 is a catheter, the needle, blunt dissector, and/or the like may be deployed as one of the instruments slideably deployed through one of the lumens of working instrument 510. Once working instrument 510 has reached target tissue 422 or point of entry 450, working instrument 510 and/or an instrument slideably deployed through one of the lumens of working instrument 510 is replaced by one or more instruments in order to perform a procedure on target tissue 422. In some examples, the one or more instruments may be consistent with medical instrument 226 and may include a biopsy instrument (such as a biopsy needle, biopsy forceps, etc.), an ablation device (such as a cryotherapeutic, RF, microwave, ultrasound, high-intensity focused ultrasound, laser, chemical delivery, or direct heat device), a drug delivery needle, and/or other surgical, diagnostic, or therapeutic tools Working instrument 510 may optionally include one or more sensors 520 located at or near a distal end of working instrument 510. In some examples, the one or more sensors 520 aid in the positioning of the working instrument 510. In some examples, the one or more sensors 520 may include one or more ultrasound transducers, such as forward facing ultrasound transducers, which may be usable to provide one or more images that may help in guiding a distal end of working instrument 510 to target tissue 422 and/or to perform the procedure on target tissue 422. In some embodiments, when working instrument 510 includes a shape sensor (such as shape sensor 222), once working instrument 510 is inserted through point of entry 450, additional knowledge regarding a location of point of entry 450 may be advantageously used to improve the registration of working instrument 510 by placing additional geometric constraints on the positioning data supplied by the shape sensor.

Figure 8A:
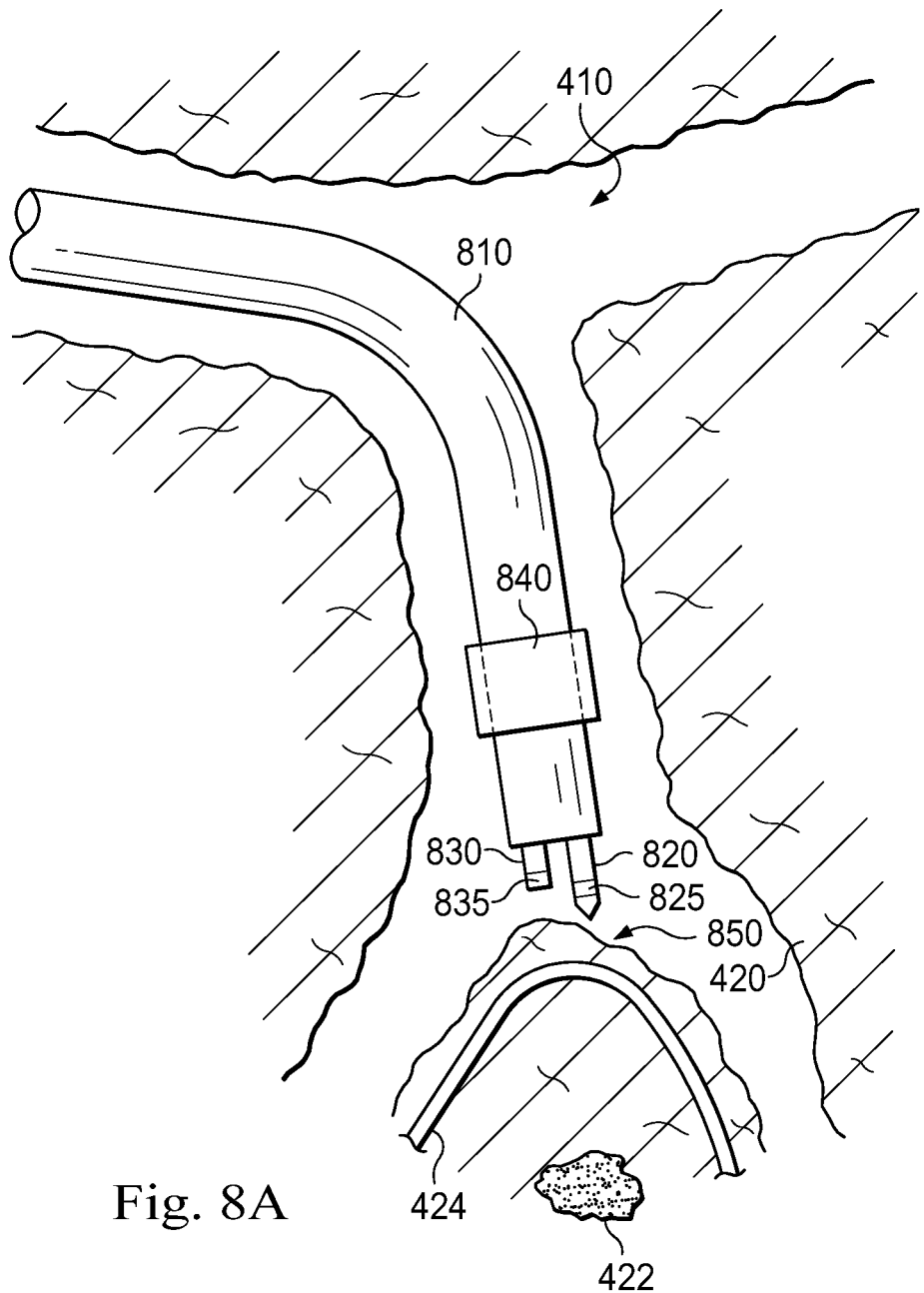
FIGS. 8A and 8B are simplified diagrams of side views of medical instruments within patient anatomy according to some additional embodiments.
Figure 8B:
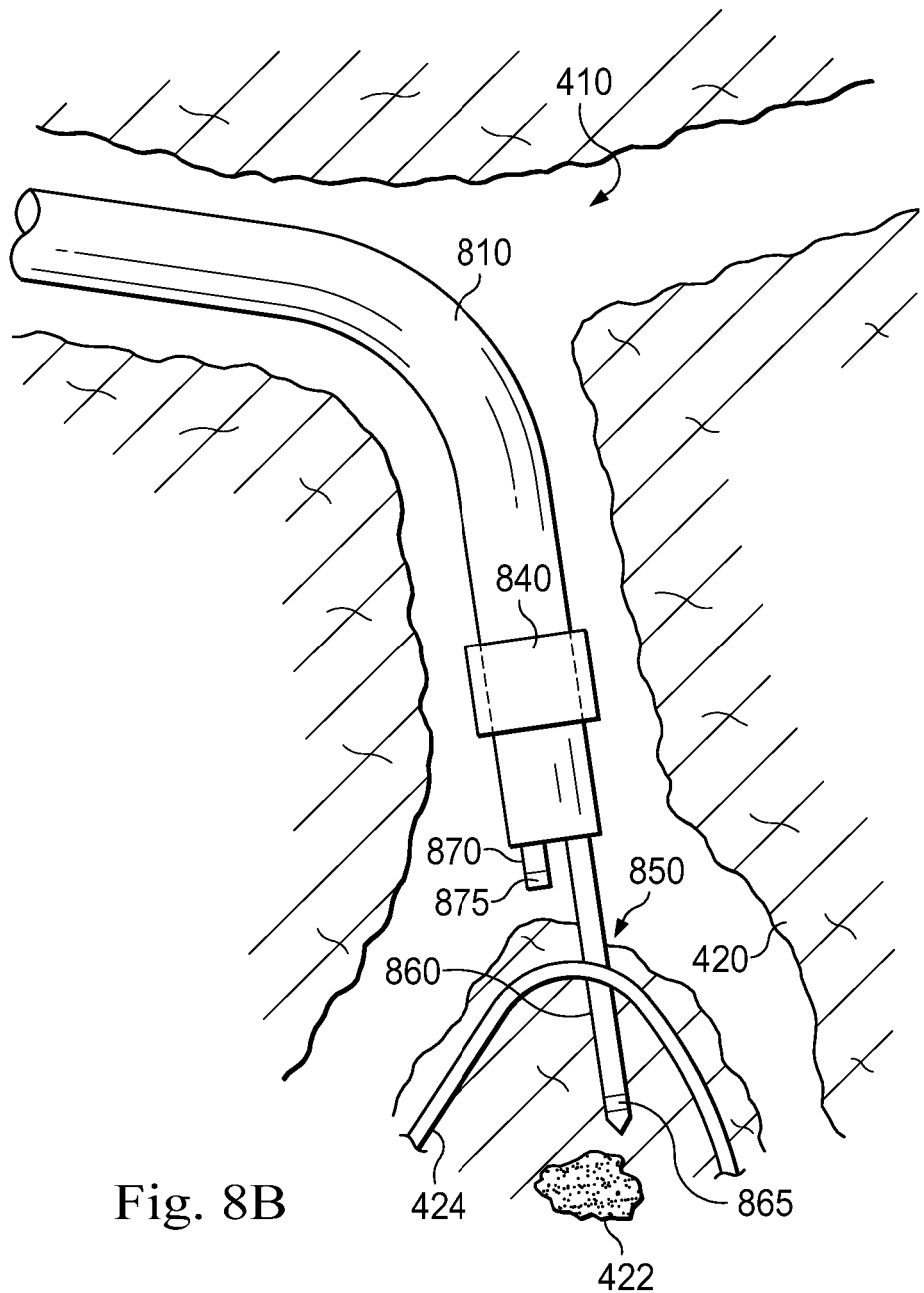

FIGS. 8A and 8B are simplified diagrams of side views of medical instruments within patient anatomy according to some additional embodiments. As shown in FIG. 8A, outer catheter 430 of FIGS. 4A, 5, 6, and 7 is replaced with an outer catheter 810 having two or more lumens (not shown). Slideably deployed through a first one of the lumens is an inner instrument 820, which may be used to penetrate tissue 420 at a point of entry 850. In some examples, inner instrument 820 may be consistent with inner instrument 440. Inner instrument 820 may optionally include one or more sensors 825 that are consistent with the one or more sensors 445 to aid in the positioning of inner instrument 820 and/or outer catheter 810 toward point of entry 850. Outer catheter 810 further includes a sealing device 840 for sealing passageways 410 at a sealing location, and sealing device 840 may be consistent with sealing device 434.

In contrast to outer catheter 430, outer catheter 810 includes at least a second lumen, which may be used to deploy a sensing probe 830 having one or more sensors 835 located near a distal end of sensing probe 830. In some examples, sensing probe 830 and the one or more sensors 835 may replace and/or supplement the one or more sensors 432 (not shown in FIG. 8A). For example, the one or more sensors 835 may include one or more imaging sensors to aid in the positioning of outer catheter 810 near point of entry 850, to aid in avoiding damage to portions of tissue 420 (such as the one or more blood vessels 424), and/or the like in much the same way as the one or more sensors 432 may be used to guide outer catheter 430. In some examples, the outer catheter 810 may not include sealing device 840. Alternatively the sealing device 840 may be included on sensing probe 830. In some examples, the distal end of sensing probe 830 may be articulated allowing the one or more sensors 835 to be better directed toward point of entry 850. In some examples, when the one or more sensors 432 are used to aid in detecting of bleeding, the one or more sensors 432 may include a fiberscope, an endoscope, and/or the like, which may use techniques such as Fourier transform infrared spectroscopy, Raman spectroscopy, and/or the like to aid in the detecting of bleeding.

As shown in FIG. 8B, a working instrument 860 is slideably deployed through a lumen in outer catheter 810 and through point of entry 850 so that a distal end of working instrument 860 is deployed to target tissue 422. Like working instrument 510, working instrument 860 may be representative of any suitable working instrument for performing a procedure on target tissue 422, may be an instrument inserted through a lumen of working instrument 820, may include one or more lumens for slideably deploying working instruments, and/or may include an optional dilation device similar to dilation device 710. Working instrument 860 may further include one or more sensors 865, which may be consistent with the one or more sensors 520. FIG. 8B further shows a sensing probe 870 having one or more sensors 875 located near a distal end of sensing probe 870. In some examples, the one or more sensors 875 may include one or more sensors that are used to aid in detecting of bleeding in much the same way that the one or more sensors 532 are used to detect bleeding. Like sensing probe 830, the distal end of sensing probe 870 may optionally be articulated. In some examples, sensing probe 870 may be sensing probe 830 and the one or more sensors 875 may be the one or more sensors 835. Although not shown, in some embodiments, both sensing probe 830 and sensing probe 870 may be simultaneously deployed toward point of entry 850 using a common lumen and/or separate lumens in outer catheter 810.

Figure 9:
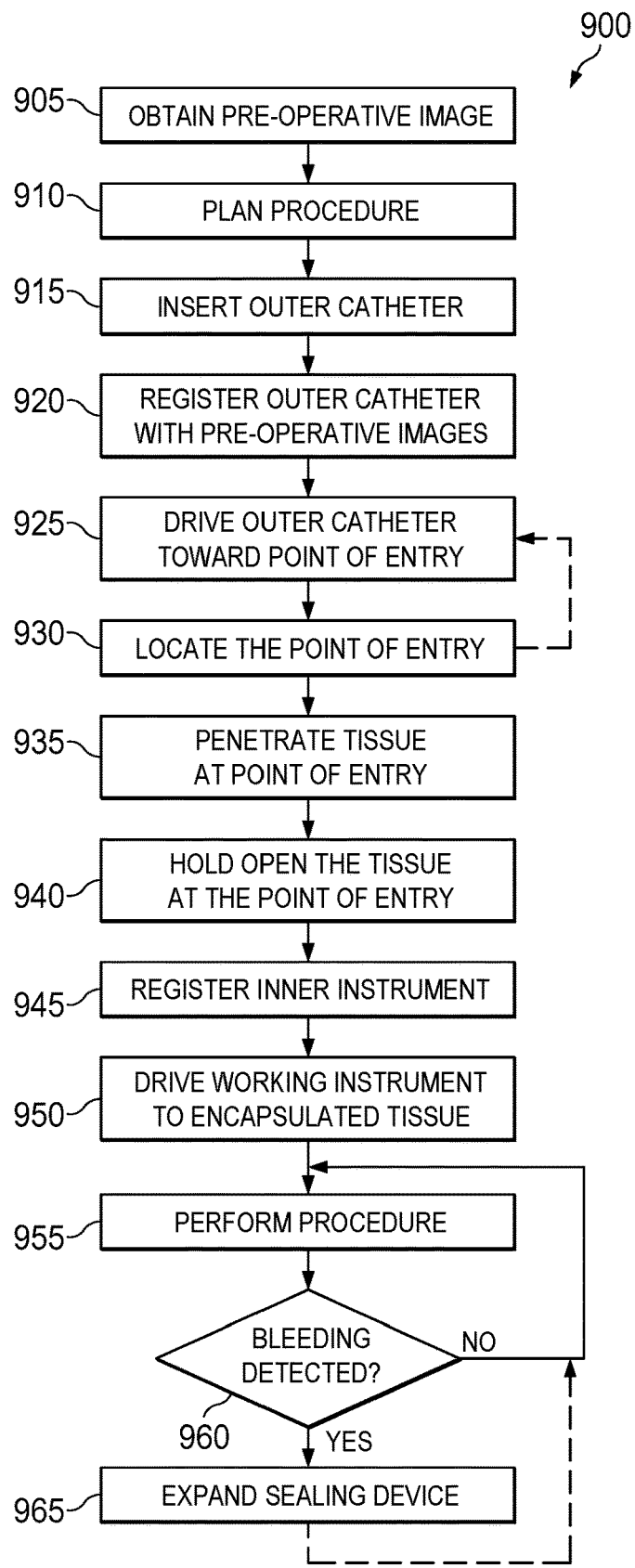
FIG. 9 is a simplified diagram of a method of performing a procedure on encapsulated tissue according to some embodiments.

FIG. 9 is a simplified diagram of a method 900 of performing a procedure on encapsulated tissue according to some embodiments. One or more of the processes 905-965 of method 900 may be implemented, at least in part, in the form of executable code stored on non-transient, tangible, machine readable media that when run by one or more processors (e.g., one or more processors of control system 112) may cause the one or more processors to perform one or more of the processes 905-965. In some embodiments, method 900 is usable to manipulate one or more medical instruments, such as any of the instruments discussed above with respect to FIGS. 2, 4A, and/or 5-8B, to perform a procedure where target anatomy that includes encapsulated tissue, such as target tissue 422, may not be directly accessed from an anatomic passageway. The ordering of processes 905-965 in FIG. 9 is exemplary only and other possible orderings and/or arrangements of processes 905-965 are possible. In some examples, one or more of processes 905-965 may be performed concurrently. In some examples, processes 960 and 965 may be performed concurrently with processes 935-955 so that bleeding may be detected and mitigating actions taken as soon as possible. In some embodiments, one or more of processes 905-965 may be optional and can be omitted. In some embodiments, other processes not shown in FIG. 9 may also be part of method 900.

At a process 905, one or more pre-operative images are obtained of a target anatomy. Using any suitable imaging technology, such as CT, MM, fluoroscopy, thermography, ultrasound, OCT, thermal imaging, impedance imaging, laser imaging, nanotube X-ray imaging, and/or the like, image data is obtained. This pre-operative image data is processed to generate one or more two-dimensional, three-dimensional, or four-dimensional (including e.g., time based or velocity based information) images. In some examples, the images may further be processed to create one or more models of the target anatomy, including locations and orientations of passageways usable to reach the target anatomy. In some examples, the target anatomy may correspond to a tumor or lesion, such as target tissue 422. In some examples, the one or more images and/or one or more models may further account for a phase of anatomic motion (e.g., respiration, heart activity, and/or the like) in order to better model changes within the target anatomy and/or the passageways due to the anatomic motion.

At a process 910, a procedure is planned using the one or more images and/or the one or more models obtained during process 905. Elements of the plan include determining paths through the passageways for each of the surgical instruments including, for example, outer catheters 430 and/or 810 and/or working instruments 440, 510, 820, and/or 860. Additional elements of the plan include determining target locations for positioning and orienting each of the surgical instruments for its intended task. In some examples, this includes determining where to place a point of entry, such as point of entry 450 and/or 850. In some examples, this further includes determining where to position and orient the distal end of an outer catheter so that it aligns with the point of entry so that a working instrument, such as working instrument 510 and/or 860 can be deployed. This further includes determining where to position and orient the one or more sensors, such as the one or more sensors 432, 445, 520, 825, 835, and/or 875 so that the procedure may be effectively and safely performed on the encapsulated tissue. Elements of the plan can additionally include determining where to position and orient a sealing device, such as sealing device 434 and/or 840, and/or a dilation device, such as dilation device 710.

At a process 915, the outer catheter is inserted into the passageways. Using, for example, instrument carriage 306 and insertion stage 308, the outer catheter is inserted into one or more passageways, such as the airways of the lungs of patient P (corresponding to passageways 410), vasculature, colon calices, kidney calices, and/or the like, and is navigated by the operator toward the target anatomy and the encapsulated tissue according to the plan determined during process 910. In some examples, navigation of the outer catheter within the passageways may be aided by an imaging device, such as an endoscope and/or the one or more sensors 432 and/or 835, providing images from the distal end of the outer catheter.

At a process 920, the outer catheter is registered to the preoperative images and/or models obtained during process 905. As the outer catheter is inserted into and moved around the passageways, position and orientation data for the outer catheter and the distal end of the outer catheter are gathered using, for example, tracking system 230, shape sensor 222, and/or position sensor system 220. As this position and orientation data is collected, it is correlated with the similar position and orientation data on the passageways determined using the one or more models obtained during process 905. Once sufficient position and orientation data for the outer catheter and/or the distal end are obtained, a registration transform is developed that maps position and orientation data obtained for the outer catheter and the distal end into the models obtained during process 905. This registration transform is typically suitable to address position, scaling, and/or orientation differences between the actual patient anatomy navigated by the outer catheter and the distal end and the model data for the same patient anatomy obtained during process 905. For example U.S. Pat. No. 8,900,131 (filed May 13, 2011 and issued Dec. 2, 2014) (disclosing "Medical System Providing Dynamic Registration of a Model of an Anatomic Structure for Image-Guided Surgery") which is incorporated by reference herein in its entirety, discloses several approaches for performing such a registration. In some examples, the shape sensor and/or the position detection system may further be used to develop a kinematic model that tracks the position and orientation of the distal end relative to a proximal end of the outer catheter. In some examples, the proximal end may correspond to a known point on instrument carriage 306 and/or insertion stage 308 used to insert and/or retract the outer catheter within the passageways.

At a process 925, the outer catheter is driven toward the point of entry using the one or more plans determined during process 910 and the registration of process 920. As the outer catheter is driven, additional position and orientation data obtained using the shape sensor and/or position sensor system may be used to continually monitor the position and orientation of the distal end of the outer catheter relative to the passageways and the point of entry. In some examples, navigation of the outer catheter within the passageways may be aided by an imaging device, such as an endoscope, providing images from the distal end of the outer catheter. In some examples, information from the one or more plans obtained during process 910 may be used to provide guidance to the operator using haptic feedback and/or a display system, such as display system 110, by providing directional hints, virtual overlays, and/or the like.

At a process 930, the point of entry is located. Using one or more sensors, such as the one or more sensors 432, 445, 825, and/or 835, are used to locate the point of entry near the target anatomy and the encapsulated tissue. For example, OCT, Doppler OCT, and/or ultrasonic sensors may be used to locate the point of entry based on surface features of the point of entry and/or based on the locations of one or more sub-surface anatomical features for which contact and/or penetration should be avoided, such as the one or more blood vessels 424. In some examples, the preoperative images of process 905 and/or the registration of process 920 may be used to help locate the point of entry.

In some examples, processes 925 and 930 may be performed concurrently and/or in a repeating cycle until a point of entry that provides access to the encapsulated tissue and avoids the one or more sub-surface anatomical features for which contact and/or penetration should be avoided. During the cycle of processes 925 and 930 feedback may be provided to the operator to help guide the operator in locating the point of entry and positioning and orienting the outer catheter toward the point of entry. In some examples, the feedback may include one or more audio, visual, and/or haptic feedback cues. Once the outer catheter is positioned and oriented toward the point of entry as desired for the rest of the procedure, the outer catheter is parked. The parking positions the outer catheter within the passageways so that it is not further inserted and/or retracted within the passageways. In some examples, a stiffness of the outer catheter may further be increased so that the outer catheter is further held in position within the passageways.

At a process 935, tissue at the point of entry is penetrated. Using a needle, a blunt dissector, and/or the like, such as the needle or blunt dissector of inner instrument 440 and/or 820, the surface of the passageway at the point of entry is penetrated. In some examples, the needle or blunt dissector may by advanced out of a lumen of the outer catheter and/or out of a lumen of the inner instrument (which is slideably deployed through the lumen of the outer catheter) along a path between the distal end of the outer catheter and the encapsulated tissue. In some embodiments, when process 930 determines that one or more sub-surface anatomical features cannot be suitably avoided should the needle or blunt dissector of the inner instrument be advanced into the point of entry, performance of process 935 may be automatically blocked.

At a process 940, the tissue at the point of entry is held open. The tissue at the point of entry may be held open by keeping the inner instrument in place after the point of entry is penetrated. In some examples, when inner instrument is an inner catheter this may include leaving the inner catheter in place through the point of entry and using a lumen within the inner catheter to deploy one or more additional working instruments, such as any of the inner instruments 510 and/or 860, along the path toward the encapsulated tissue. In some embodiments, when the inner instrument is equipped with a dilation device, such as dilation device 710, the dilation device may be enlarged and/or expanded to further hold the point of entry open and/or to additionally stabilize the inner instrument within the point of entry. The dilation device may be expanded by injecting air, saline, and/or some other gas or fluid into the one or more balloons forming the dilation device.

At an optional process 945, the inner instrument is registered. Once the inner instrument is inserted through the point of entry, additional knowledge regarding a location of the point of entry may be advantageously used to further register the inner instrument to the one or more preoperative images and/or models obtained during process 905. The further registration is possible because position information about the point of entry may provide one or more geometric constraints on positioning data supplied by a shape sensor, such as shape sensor 222, on the inner instrument. This is possible because positioning error of the shape sensor typically increases with distal distance from a known proximal point on the shape sensor. Thus, knowledge that the shape sensor passes through the point of entry generally allows for a more accurate location of the point on the shape sensor that passes through the point of entry than may be obtained via the position determined relative to the known proximal point of the shape sensor.

At a process 950, the working instrument is driven to the encapsulated tissue. Using a needle, a blunt dissector, and/or the like located at the distal end of the working instrument, the distal end of the working instrument may be further penetrated through the tissue along the path between the point of entry and the encapsulated tissue until the distal end of the working instrument reaches the encapsulated tissue. In some examples, the working instrument may be further penetrated through the tissue by further extending the working instrument beyond the distal end of the outer catheter and/or further extending the needle and/or blunt dissector beyond the distal end of the inner instrument when the inner instrument is also a catheter. In general the path between the point of entry and the encapsulated tissue is a straight line, however, when the working instrument is steerable like elongate device 202, the path between the point of entry and the encapsulated tissue may include one or more bends and/or curves.

At a process 955, a procedure is performed. Once the distal end of the working instrument reaches the encapsulated tissue, the procedure may be performed. In some examples, the procedure may be performed using the distal end of the working instrument and/or may be performed using one or more instruments slideably deployed through a lumen in the working instrument. In some examples, the working instrument and/or the one or more instruments may be consistent with medical instrument 226 and may include a biopsy instrument (such as a biopsy needle, biopsy forceps, etc.), an ablation device (such as a cryotherapeutic, RF, microwave, ultrasound, high-intensity focused ultrasound, laser, chemical delivery, or direct heat device), a drug delivery needle, and/or other surgical, diagnostic, or therapeutic tools as appropriate for the procedure being performed.

At a process 960, it is determined whether bleeding is detected. Using one or more sensors, such as the one or more sensors 432 and/or 875, the passageways between the distal end of the outer catheter and the point of entry are monitored to determine whether penetration of the tissue at the point of entry and/or advancement of the working instrument toward the encapsulated tissue has resulted in undesirable and/or excessive bleeding. For example, the bleeding may be caused by damage caused to one or more blood vessels, such as the one or more blood vessels 424. When undesirable or excessive bleeding is detected, a sealing device may be expanded using a process 965. When acceptable or no bleeding is detected processes 955 and/or 960 are repeated to allow the distal end of the working instrument to be further driven toward the encapsulated tissue and/or for the procedure to continue.

At the process 965, the sealing device, such as the sealing device 434 and/or 840 is expanded to create a barrier between the point of entry and the proximal portions of the passageways. The sealing device may be expanded by injecting air, saline, and/or some other gas or fluid into the one or more balloons forming the sealing device. In some embodiments, expansion of the sealing device to seal the passageway is manually activated by the operator in response to an alarm (visual and/or audio) triggered by automatic detection of the bleeding during process 960 and/or automatically in response to the automatic detection of the bleeding during process 960. Once the sealing device is expanded and the passageway sealed, continued driving of the working instrument toward the encapsulated tissue and/or performance of the procedure during processes 950 and 955, respectively, may be permitted to continue at the discretion of the operator.

Although not expressly shown in FIG. 9, process 960 may further include a determination whether damage is caused to pleural tissue resulting in an increased likelihood of a pneumothorax. When damage to the pleural tissue is detected, the sealing device may be manually and/or automatically expanded using process 965.

One or more elements in embodiments of the invention (e.g., method 900) may be implemented in software to execute on a processor of a computer system, such as control system 112. In some examples, the software may be included on non-transient, tangible, machine readable media that includes executable code that when run by one or more processors may cause the one or more processors to perform the processes of method 900. Some common forms of machine readable media that may include the processes of method 900 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read. In some examples, the software may be downloaded via computer networks such as the Internet, Intranet, etc. As described herein, operations of accessing, detecting, initiating, registered, displaying, receiving, generating, determining, moving data points, segmenting, matching, etc. may be performed at least in part by the control system 112 or the processors thereof.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A medical system for performing a minimally invasive procedure within an anatomic passageway, the system comprising:
an outer catheter comprising one or more first lumens;
a sealing device coupled to the outer catheter;
an inner instrument configured to be slideably deployed through one of the one or more first lumens;
one or more first sensors; and
a processor configured to:
detect bleeding into the anatomic passageway from outside the anatomic passageway using the one or more first sensors, wherein the one or more first sensors are configured to be positioned distal to the sealing device, at least one of the one or more first sensors being mounted near a distal end of the outer catheter, on a sensing probe deployed through one of the one or more first lumens, or near a distal end of the inner instrument;
wherein the inner instrument comprises one or more second sensors mounted near a distal end of the inner instrument configured to be positioned at a location distal to the one or more first sensors, the one or more second sensors being configured to detect one or more features below a surface of the anatomic passageway near a point of entry, the one or more features including at least one of target tissue, one or more blood vessels, or lung pleural tissue, wherein the processor is further configured to disable advancement of the inner instrument when the one or more second sensors detect the one or more features.

2. The system of claim 1, wherein at least one of the outer catheter or the inner instrument further comprises a tracking system, wherein the tracking system includes at least one of a fiber optic shape sensor or an EM sensor.

3. The system of claim 1, wherein the inner instrument comprises a distal end shaped for penetrating a surface of the anatomic passageway at a point of entry.

4. The system of claim 1, wherein the inner instrument comprises a biopsy device, an ablation device, or a drug delivery needle.

5. The system of claim 1, wherein the inner instrument comprises one or more second lumens, wherein a working instrument is configured to be slideably received through the one or more second lumens.

6. The system of claim 5, wherein the inner instrument or the working instrument comprises a dilation device for expanding an opening in a surface of the anatomic passageway at a point of entry.

7. The system of claim 1, wherein the one or more first second sensors comprise at least one of an imaging sensor, a Doppler OCT device, or a Doppler ultrasound device.

8. The system of claim 7, wherein the imaging sensor comprises a fiberscope, an endoscope, a fiber optic bundle, an OCT device, or an ultrasound transducer.

9. The system of claim 1, wherein the processor is further configured to:
perform, in response to detecting the bleeding into the anatomic passageway, at least one of issuing an audio alert or issuing a visual alert.

10. The system of claim 1, wherein the sealing device comprises one or more balloons.

11. The system of claim 1, wherein:
the sealing device comprises a balloon catheter configured to be deployed through the one or more first lumens or the sealing device is mounted to a sheath surrounding the outer catheter.

12. The system of claim 1, wherein at least one of the outer catheter or the inner instrument is steerable.

13. A method of performing a procedure on a target anatomical tissue, the method comprising:
detecting, by a processor, blood which has entered an anatomic passageway using one or more first sensors mounted on a medical system, wherein the medical system is positioned within the anatomic passageway;
activating, by the processor, a sealing device mounted on the medical system to seal the anatomic passageway at a sealing location, wherein the activating of the sealing device occurs in response to detecting the blood which has entered the anatomic passageway, wherein the one or more first sensors are positioned distal to the sealing device, at least one of the one or more first sensors being mounted near a distal end of an outer catheter of the medical system, on a sensing probe configured to be deployed through the outer catheter, or near a distal end of an inner instrument configured to be deployed through the outer catheter;

detecting one or more anatomical features below a surface of the anatomic passageway using one or more second sensors mounted to the medical system; and disabling advancement of the medical system when the one or more second sensors detect the one or more anatomical features.

14. The method of claim 13, further comprising inflating a dilation device to expand an opening, wherein the opening is created by the medical system at a surface of the anatomic passageway at a point of entry and the dilation device is mounted on the medical system.

15. The method of claim 13, further comprising delivering, using the medical system, at least one of ablative energy or drugs to treat the target anatomical tissue.

16. A medical system for performing a minimally invasive procedure within an anatomic passageway, the system comprising:

an outer catheter comprising one or more first lumens;
a sealing device coupled to the outer catheter;
an inner instrument configured to be slideably deployed through one of the one or more first lumens and comprising one or more first sensors configured to detect one or more anatomical features below a surface of the anatomic passageway;
one or more second sensors; and
a processor configured to:
detect bleeding into the anatomic passageway from outside the anatomic passageway using the one or more second sensors, wherein the one or more second sensors are configured to be positioned distal to the sealing device and mounted on the inner instrument near a distal end of the inner instrument; and
disable advancement of the inner instrument when the one or more first sensors detect the one or more anatomical features.

17. The system of claim 1, wherein the processor and the one or more second sensors are configured to detect the bleeding into the anatomic passageway using spectroscopy.

18. The system of claim 1, wherein the one or more second sensors comprise Doppler devices configured to detect motion of blood.

19. The system of claim 18, wherein the one or more second sensors comprise optical coherence tomography sensors.

* * * * *

UNITED STATES PATENT AND TRADEMARK OFFICE
CERTIFICATE OF CORRECTION

PATENT NO. : 12,161,306 B2
APPLICATION NO. : 16/484047
DATED : December 10, 2024
INVENTOR(S) : Stephen J. Blumenkranz, Federico Barbagli and Christopher R. Carlson Page 1 of 1

It is certified that error appears in the above-identified patent and that said Letters Patent is hereby corrected as shown below:

In the Specification

Column 6, Line 26, change "(MM)" to -- (MRI) --

Column 19, Line 26, change "(MM)" to -- (MRI) --

Signed and Sealed this
Fourth Day of February, 2025

Coke Morgan Stewart
*Acting Director of the United States Patent and Trademark Office*